US011230610B2

(12) United States Patent
Trang et al.

(10) Patent No.: US 11,230,610 B2
(45) Date of Patent: Jan. 25, 2022

(54) BIVALENT ANTIBODIES MASKED BY COILED COILS

(71) Applicant: SEAGEN INC., Bothell, WA (US)

(72) Inventors: Vivian Trang, Bothell, WA (US); Matthew R. Levengood, Bothell, WA (US); Peter Senter, Bothell, WA (US)

(73) Assignee: SEAGEN INC., Bothell, WA (US)

( * ) Notice: Subject to any disclaimer, the term of this patent is extended or adjusted under 35 U.S.C. 154(b) by 107 days.

(21) Appl. No.: 16/348,481

(22) PCT Filed: Dec. 8, 2017

(86) PCT No.: PCT/US2017/065471
§ 371 (c)(1),
(2) Date: May 8, 2019

(87) PCT Pub. No.: WO2018/107125
PCT Pub. Date: Jun. 14, 2018

(65) Prior Publication Data
US 2019/0352428 A1 Nov. 21, 2019

Related U.S. Application Data

(60) Provisional application No. 62/432,472, filed on Dec. 9, 2016.

(51) Int. Cl.
| C07K 16/46 | (2006.01) |
| A61K 47/68 | (2017.01) |
| C07K 16/28 | (2006.01) |
| C07K 16/30 | (2006.01) |
| A61K 39/00 | (2006.01) |

(52) U.S. Cl.
CPC ........ C07K 16/468 (2013.01); A61K 47/6803 (2017.08); A61K 47/6849 (2017.08); A61K 47/6879 (2017.08); C07K 16/2809 (2013.01); C07K 16/30 (2013.01); A61K 2039/505 (2013.01); C07K 2317/31 (2013.01); C07K 2317/92 (2013.01); C07K 2319/50 (2013.01); C07K 2319/73 (2013.01)

(58) Field of Classification Search
CPC ............ C07K 2319/30; C07K 2319/70; C07K 2319/72; C07K 2319/50
USPC ..................................... 424/133.1; 530/387.3
See application file for complete search history.

(56) References Cited

U.S. PATENT DOCUMENTS

| 8,865,875 | B2 | 10/2014 | Liu et al. | |
| 10,414,814 | B2* | 9/2019 | Williams | C12N 9/6491 |
| 10,683,353 | B2* | 6/2020 | Wang | A61K 47/65 |
| 2016/0002356 | A1 | 1/2016 | Christensen et al. | |
| 2016/0009817 | A1 | 1/2016 | Wang et al. | |
| 2016/0160263 | A1 | 6/2016 | Whitney et al. | |
| 2016/0185875 | A1 | 6/2016 | Cheng et al. | |
| 2019/0185561 | A1* | 6/2019 | Gardai | C07K 16/2803 |

FOREIGN PATENT DOCUMENTS

| WO | WO 1995/011703 A1 | 5/1995 |
| WO | WO 1996/034892 A1 | 11/1996 |
| WO | WO 2001/000814 A2 | 1/2001 |
| WO | WO 2001/091798 A2 | 12/2001 |
| WO | WO 2002/074993 A1 | 9/2002 |
| WO | WO 2004/009638 A1 | 1/2004 |
| WO | WO 2004/111608 A2 | 12/2004 |
| WO | WO 2005/083431 A2 | 9/2005 |
| WO | WO 2007/024715 A2 | 3/2007 |
| WO | WO 2007/077028 A2 | 7/2007 |
| WO | WO 2007/107764 A1 | 9/2007 |
| WO | WO 2009/021754 A2 | 2/2009 |
| WO | WO 2009/024771 A2 | 2/2009 |
| WO | WO 2009/025846 A2 | 2/2009 |
| WO | WO 2010/077643 A1 | 7/2010 |
| WO | WO 2010/081173 A2 | 7/2010 |
| WO | WO 2012/025525 A1 | 3/2012 |
| WO | WO 2012/025530 A1 | 3/2012 |
| WO | WO 2012/048332 A2 | 4/2012 |
| WO | WO 2013/128194 A1 | 9/2013 |
| WO | WO 2013/148248 A1 | 10/2013 |
| WO | WO 2013/163631 A2 | 10/2013 |
| WO | WO 2013/192546 A1 | 12/2013 |
| WO | WO 2013/192550 A2 | 12/2013 |
| WO | WO 2014/052462 A2 | 4/2014 |
| WO | WO 2014/107599 A2 | 7/2014 |
| WO | WO 2014/144689 A1 | 9/2014 |
| WO | WO 2014/193973 A2 | 12/2014 |
| WO | WO 2014/197612 A1 | 12/2014 |
| WO | WO 2015/013671 A1 | 1/2015 |
| WO | WO 2015/048329 A2 | 4/2015 |
| WO | WO 2015/066279 A2 | 5/2015 |
| WO | WO 2015/116933 A2 | 8/2015 |
| WO | WO 2016/004383 A1 | 1/2016 |
| WO | WO 2016/118629 A1 | 7/2016 |
| WO | WO 2016/149201 A2 | 9/2016 |
| WO | WO 2016/179257 A2 | 11/2016 |
| WO | WO 2016/179285 A1 | 11/2016 |

(Continued)

OTHER PUBLICATIONS

Trang et al. (Nature Biotech Jul. 2019;37(7):761-765; Epub May 27, 2019).*

(Continued)

Primary Examiner — Lynn A Bristol

(74) Attorney, Agent, or Firm — Alston & Bird LLP

(57) ABSTRACT

The invention provides bivalent antibodies including two light and heavy chain pairs. The N-termini of one or both light and heavy chain pairs are linked via linkers comprising a protease cleavage site to coiled-coil forming peptides that associate to form a coiled coil reducing binding affinity of at least one light-heavy chain pair to a target.

20 Claims, 15 Drawing Sheets

Specification includes a Sequence Listing.

(56) References Cited

FOREIGN PATENT DOCUMENTS

| WO | WO 2016/179335 A1 | 11/2016 |
| WO | WO 2017/011580 A2 | 1/2017 |
| WO | WO 2018/107125 A1 | 6/2018 |

OTHER PUBLICATIONS

Trang et al. (Cancer Research, (Jul. 2018) vol. 78, No. 13, Supp. Supplement 1. Abstract No. 750. Meeting Info: 2018 Annual Meeting of the American Association for Cancer Research, AACR 2018. Chicago, IL, United States. Apr. 14, 2018-Apr. 18, 2018).*
Arndt et al., "Comparison of In Vivo Selection and Rational Design of Heterodimeric Coiled Coils," Structure, 10:1235-1248, (2002).
Ratnikov et al., "Basis for substrate recognition and distinction by matrix metalloproteinases," PNAS, pp. E4148-E4155, (2014).
Schmidt, "Engineering Antibodies for improved Targeting of Solid Tumors," Massachusetts Institute of Technology, Doctoral Thesis, 154 pages, (2009).
Turk et al., "Determination of protease cleavage site motifs using mixture-based oriented peptide libraries," Nature Biotechnology, 19:661-667, (2001).
WIPO Application No. PCT/US2017/065471, PCT International Preliminary Report on Patentability dated Jun. 11, 2019.
WIPO Application No. PCT/US2017/065471, PCT International Search Report and Written Opinion of the International Searching Authority dated Feb. 16, 2018.
EP Application No. 17879207.3 (Published as EP3551667), Supplementary European Search Report and European Search Opinion dated May 20, 2020.

* cited by examiner

Fig. 1B Coiled Coils with N-terminal cysteine

CM11 CC  Light -EACGALEIRAAFLRQRNTALRTEVAELEQEVQRLENEVSQYETRYSGGGGGPLG*VRGGGGS
         Heavy -EACGALEIEAAFLERENTALETRVAELRQRVQRARNRVSQYRTRYSGGGGGPLG*VRGGGGS <u>MMP2 Sequence</u> over the region SQYETRYSGGGGGPLG*VRGGGGS CM15 CC  Light-EACGALEIEAAFLEQENTALETEVAELEQEVQRLENIVSQYETRYSGGGGGPLG*VRGGGGS
         Heavy EACGALEIRAAFLRRRNTALRTRVAELRQRVQRLRNIVSQYETRYSGGGGGPLG*VRGGGGS <u>MMP2 Sequence</u>

CVel CC  Light -EACGASTTVAQLEEKVKTLRAENYELKSEVQRLEEQVAQLGSIPVS*LRSG
         Heavy -EACGASTSVDELQAEVDQLEDENYALKTKVAQLRKKVEKLGSIPVS*LRSG <u>MMP2 sequence (IPV)</u>

Fig. 2: Concentrations of antibodies versus time for various coiled coil masked antibodies incubated in plasma as compared with an hBU12ec control.
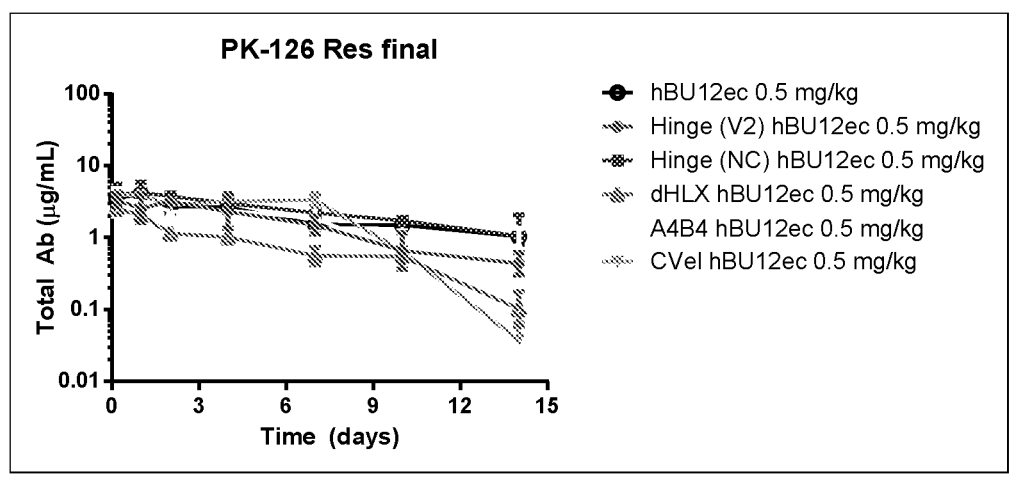

Fig. 3: In vivo zymography
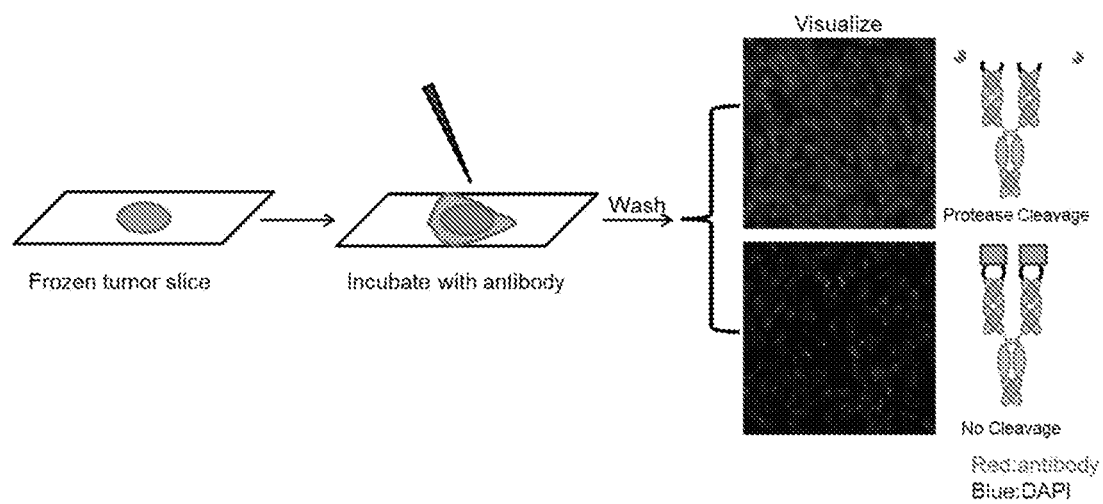

Figs. 6A-B
A
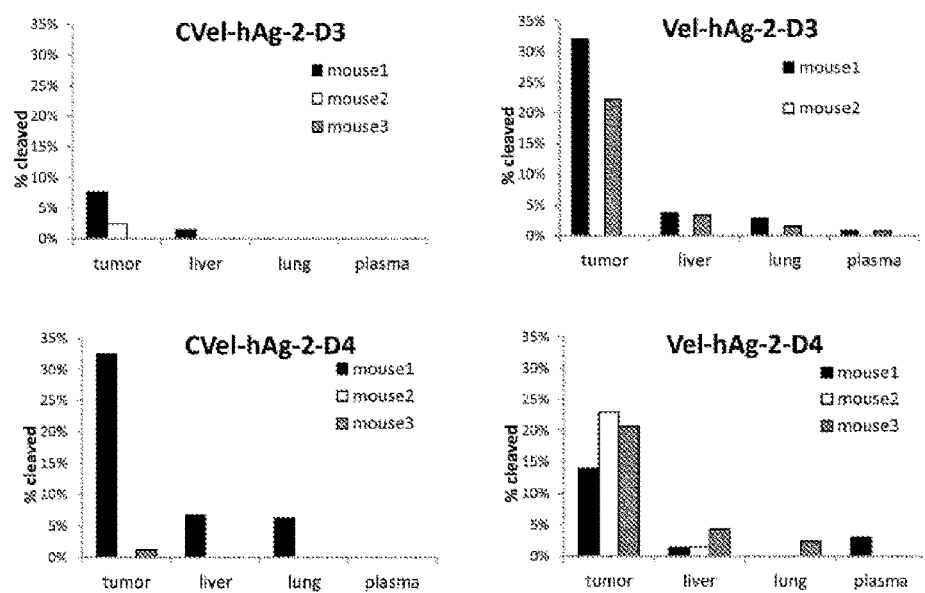
B
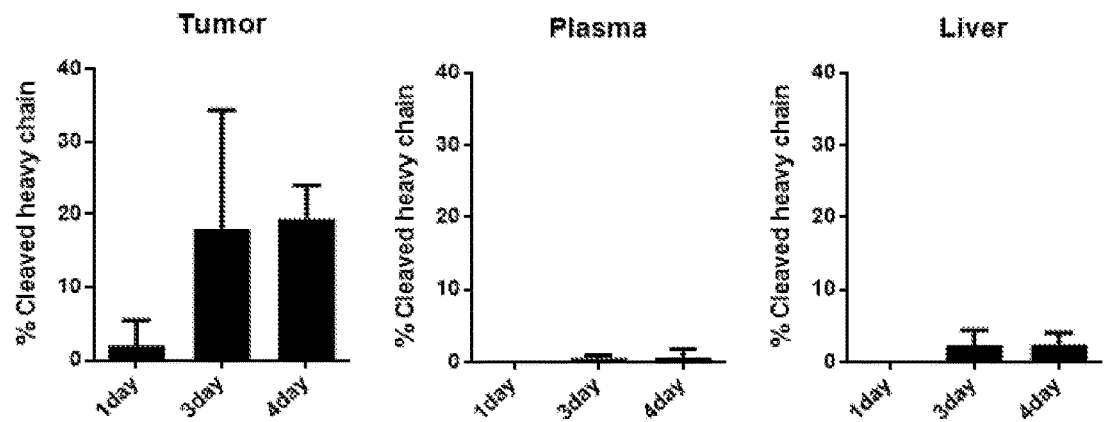

Figs. 7A-C Comparison of CVel to Vel masked anti-Ag2 antibodies
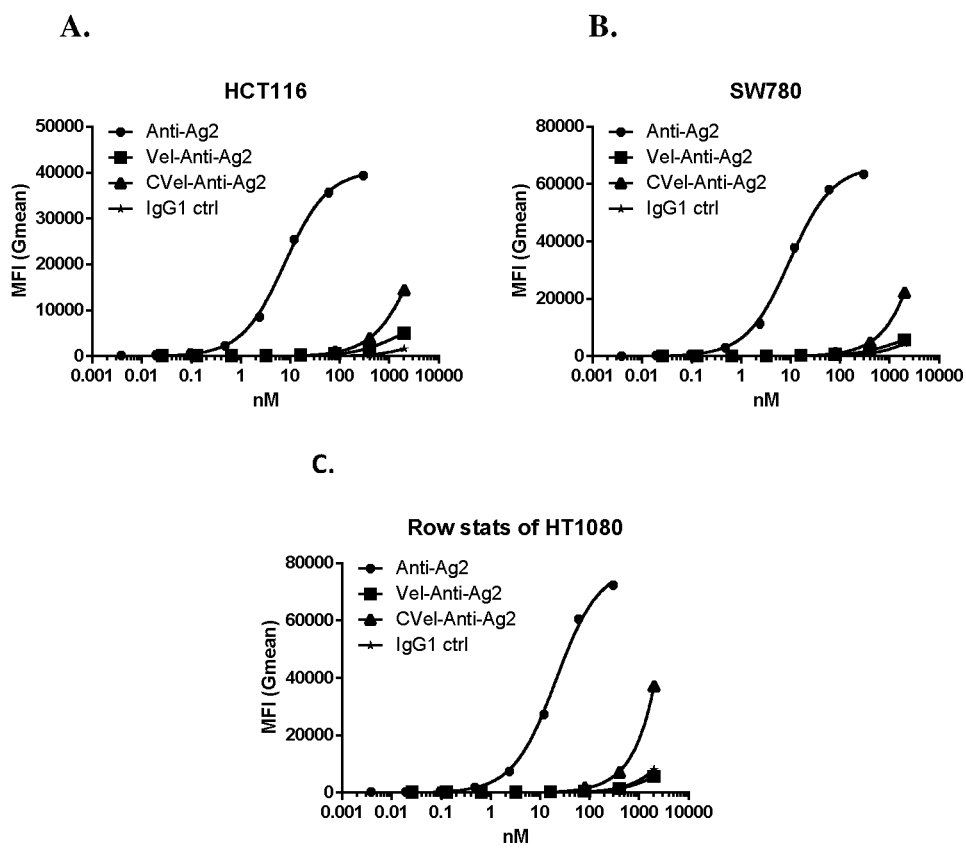

Figs. 8A-C. Comparison of unmasked and Vel-masked anti-CD19 ADCs with varying cleavage sequences
A.
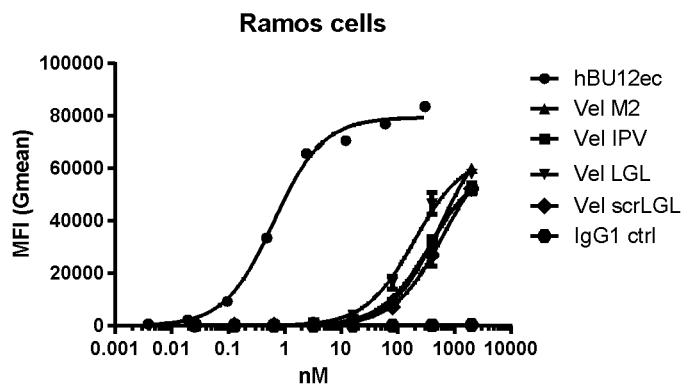
B.
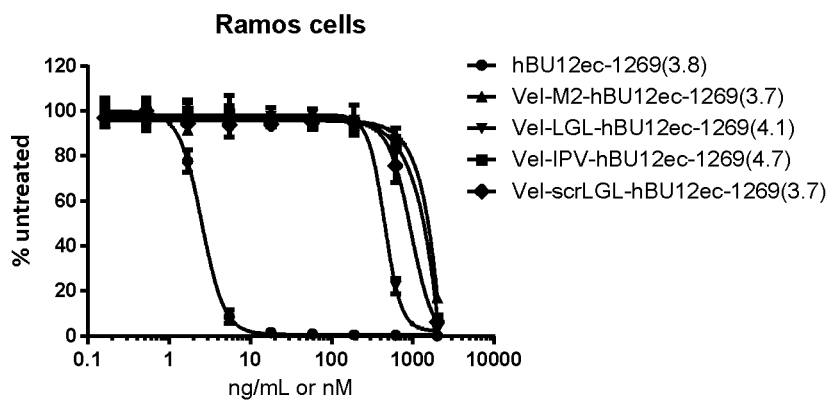
C.
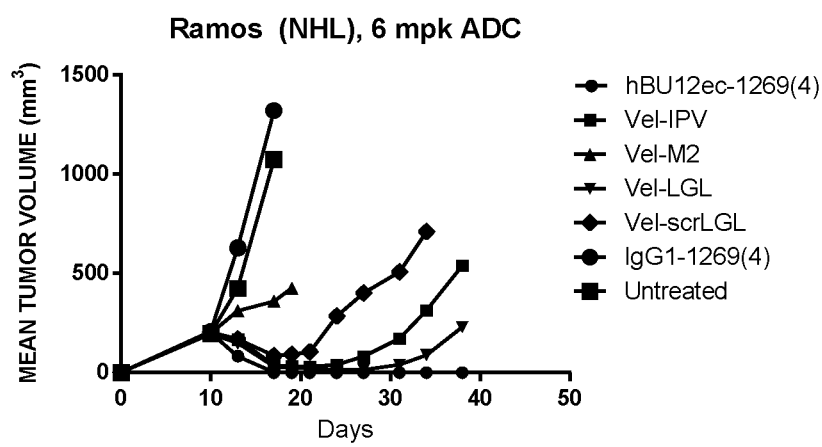

Figs. 9A-D Comparison of unmasked and masked anti-mouse CD3 antibody 145-2C11
A.
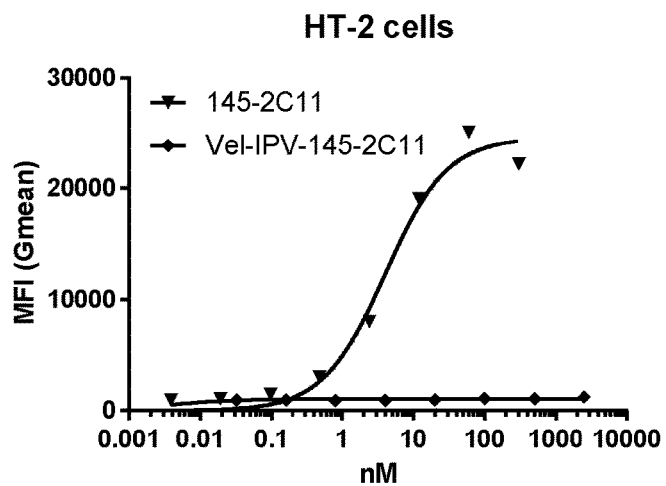
B.
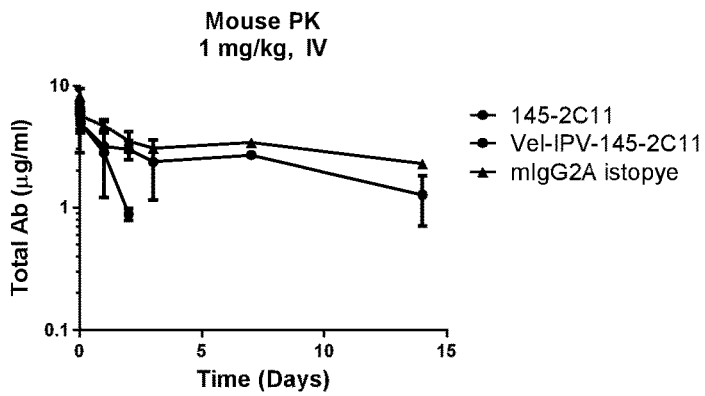
C.                    D.
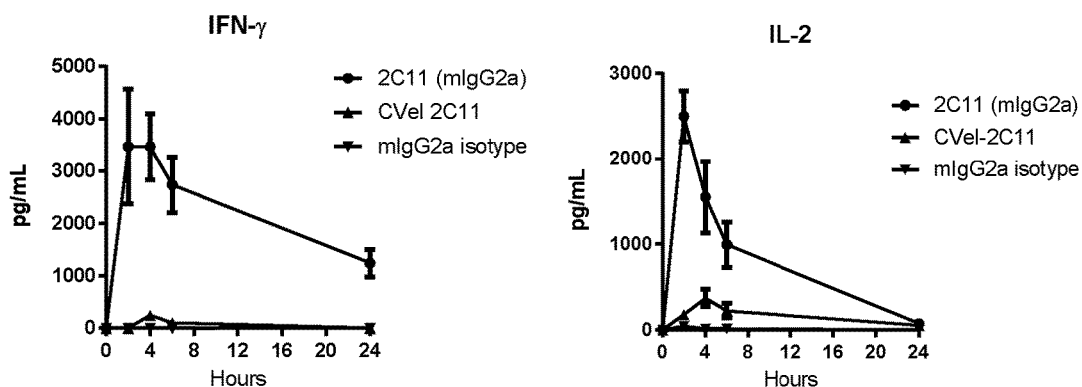

Fig 10. The stability study of masked anti-human Ag2 antibodies with different coiled coil domains Figs. 11 A-C
A.
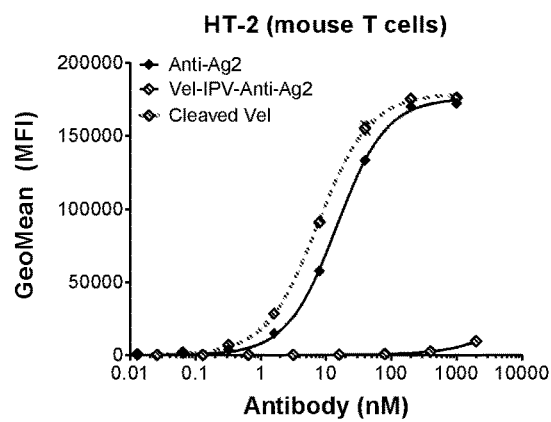
B.
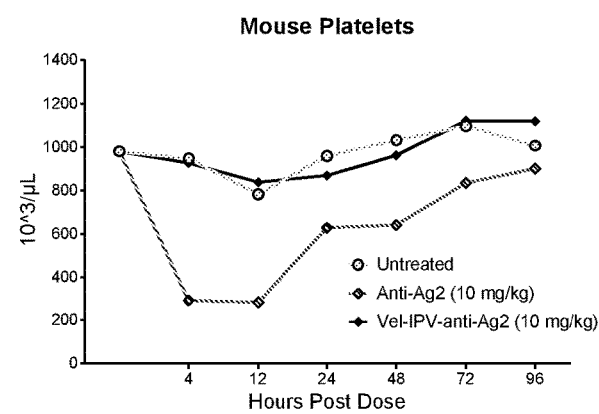
C.
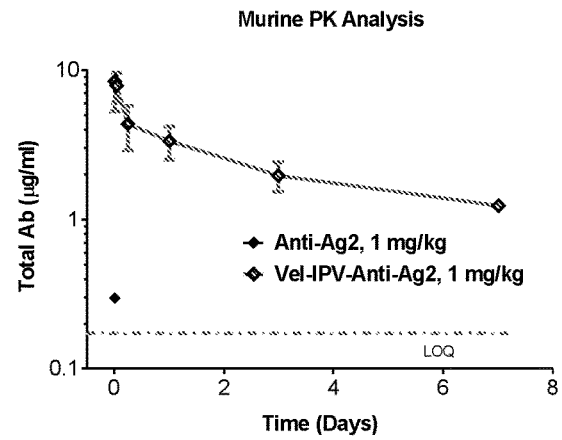

Figs. 12A-D
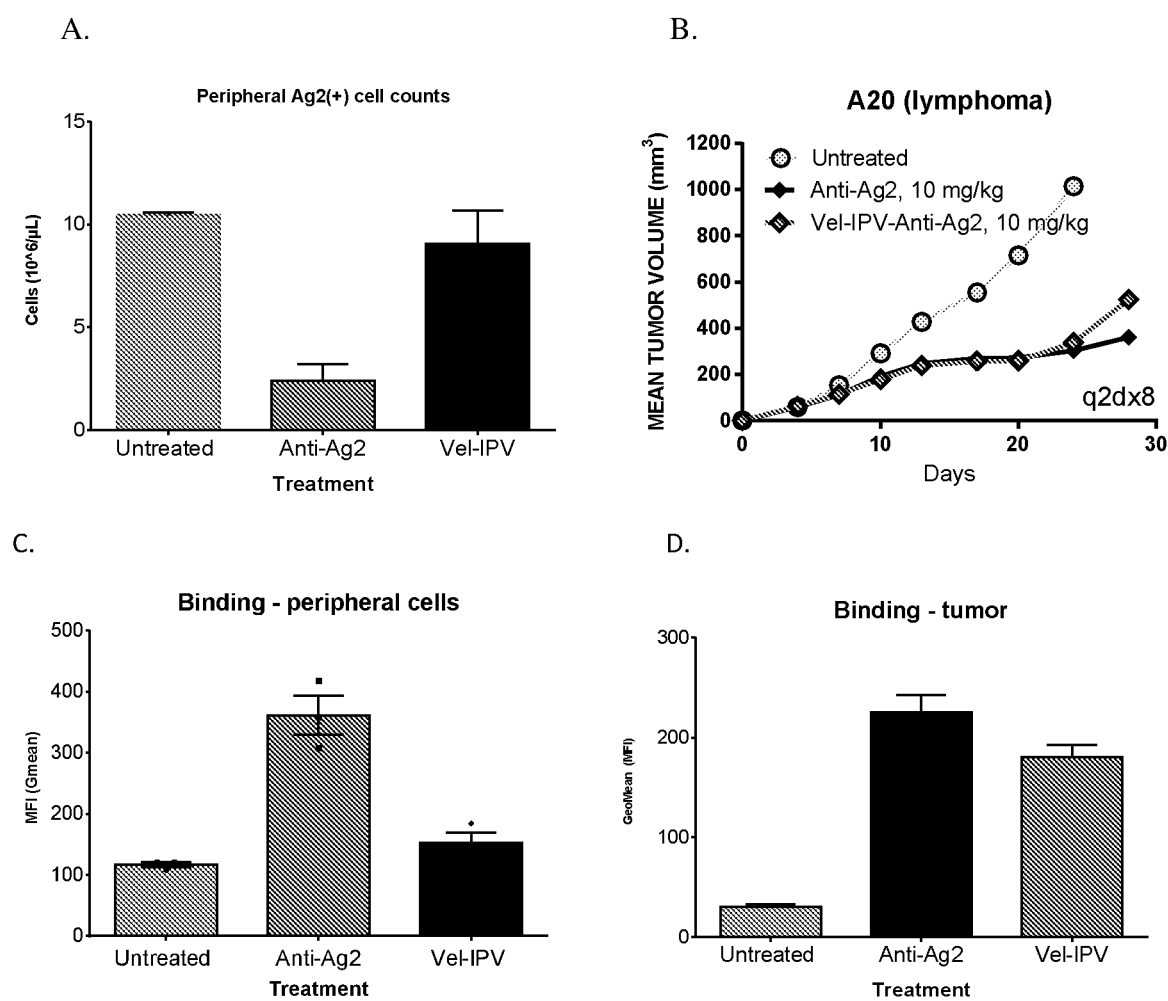

Figs. 13A-C.
A.
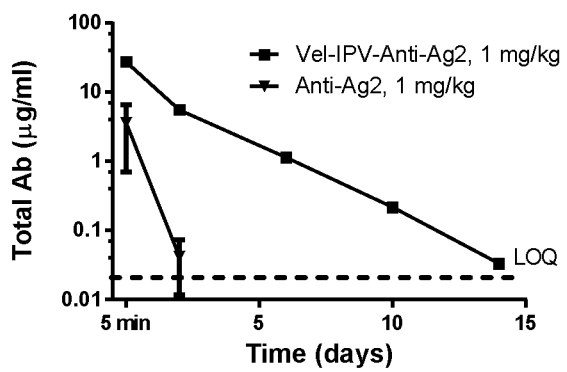
B.
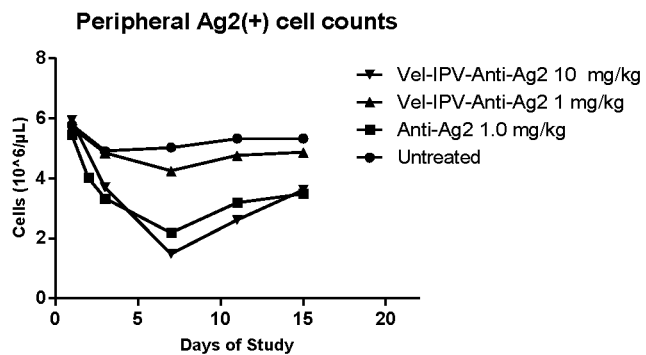
C.
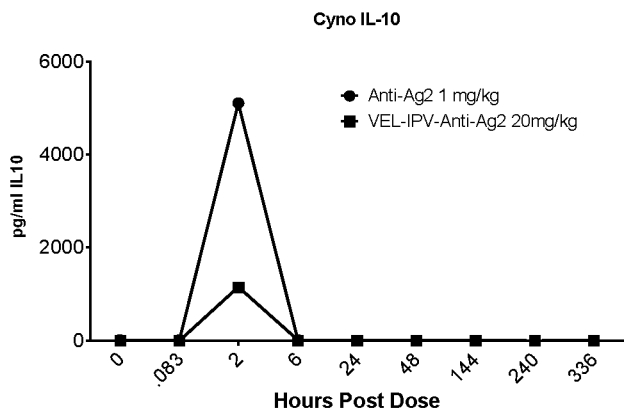

Figs. 14A and B.
A.
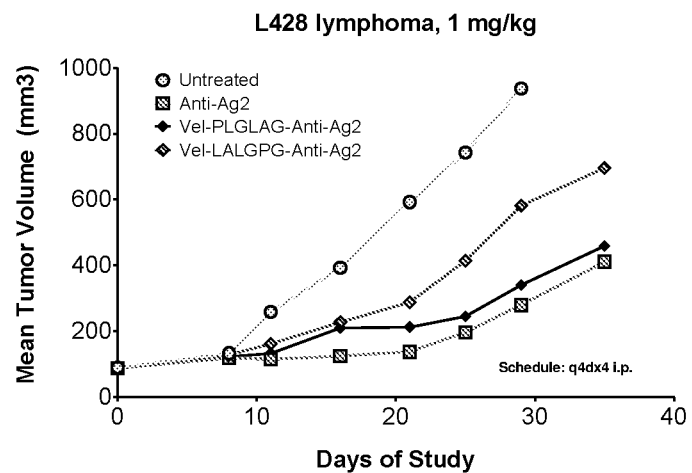
B.
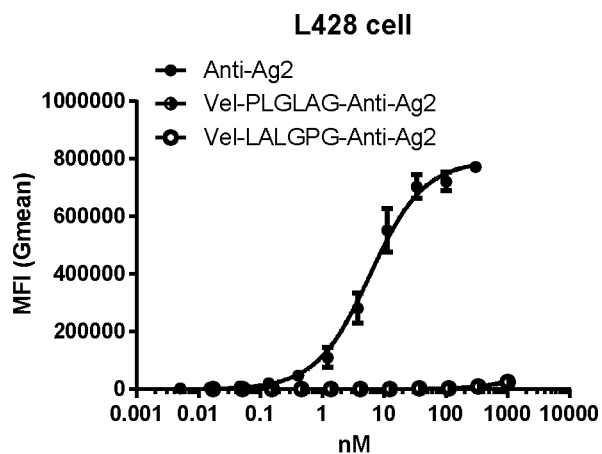

SEQUENCE LISTING

```
<160> NUMBER OF SEQ ID NOS: 84

<210> SEQ ID NO 1
<211> LENGTH: 107
<212> TYPE: PRT
<213> ORGANISM: Artificial sequence
<220> FEATURE:
<223> OTHER INFORMATION: Synthesized

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 2
<211> LENGTH: 123
<212> TYPE: PRT
<213> ORGANISM: Artificial sequence
<220> FEATURE:
<223> OTHER INFORMATION: Synthesized

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
```

```
            35                  40                  45
Ala Val Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Thr Leu Val Arg Gly Ala Met Tyr Gly Thr Asp Val
            100                 105                 110
Trp Gly Gln Gly Thr Thr Val Thr Val Ser Ser
            115                 120
```

<210> SEQ ID NO 3
<211> LENGTH: 120
<212> TYPE: PRT
<213> ORGANISM: Artificial sequence
<220> FEATURE:
<223> OTHER INFORMATION: Synthesized

<400> SEQUENCE: 3

```
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Thr Ser
             20                  25                  30
Gly Met Gly Val Gly Trp Ile Arg Gln His Pro Gly Lys Gly Leu Glu
         35                  40                  45
Trp Ile Gly His Ile Trp Trp Asp Asp Lys Arg Tyr Asn Pro Ala
     50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Met Glu Leu Trp Ser Tyr Tyr Phe Asp Tyr Trp Gly Gln
            100                 105                 110
Gly Thr Leu Val Thr Val Ser Ser
            115                 120
```

<210> SEQ ID NO 4
<211> LENGTH: 107
<212> TYPE: PRT
<213> ORGANISM: Artificial sequence
<220> FEATURE:
<223> OTHER INFORMATION: Synthesized

<400> SEQUENCE: 4

```
Glu Ile Val Leu Thr Gln Ser Pro Ala Thr Leu Ser Leu Ser Pro Gly
 1               5                  10                  15
Glu Arg Ala Thr Leu Ser Cys Ser Ala Ser Ser Ser Val Ser Tyr Met
             20                  25                  30
His Trp Tyr Gln Gln Lys Pro Gly Gln Ala Pro Arg Leu Leu Ile Tyr
         35                  40                  45
Asp Thr Ser Lys Leu Ala Ser Gly Ile Pro Ala Arg Phe Ser Gly Ser
     50                  55                  60
Gly Ser Gly Thr Asp Phe Thr Leu Thr Ile Ser Ser Leu Glu Pro Glu
 65                  70                  75                  80
Asp Val Ala Val Tyr Tyr Cys Phe Gln Gly Ser Val Tyr Pro Phe Thr
                 85                  90                  95
```

```
Phe Gly Gln Gly Thr Lys Leu Glu Ile Lys Arg
            100                 105
```

<210> SEQ ID NO 5
<211> LENGTH: 107
<212> TYPE: PRT
<213> ORGANISM: Artificial sequence
<220> FEATURE:
<223> OTHER INFORMATION: Synthesized

<400> SEQUENCE: 5

```
Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105
```

<210> SEQ ID NO 6
<211> LENGTH: 117
<212> TYPE: PRT
<213> ORGANISM: Artificial sequence
<220> FEATURE:
<223> OTHER INFORMATION: Synthesized

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
        115
```

<210> SEQ ID NO 7
<211> LENGTH: 106
<212> TYPE: PRT
<213> ORGANISM: Homo sapiens

<400> SEQUENCE: 7

```
Thr Val Ala Ala Pro Ser Val Phe Ile Phe Pro Pro Ser Asp Glu Gln
1               5                   10                  15
```

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 9
<211> LENGTH: 329
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

```
            325

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 329
<212> TYPE: PRT
<213> ORGANISM: Homo sapiens
```

-continued

```
<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 12
<211> LENGTH: 120
<212> TYPE: PRT
<213> ORGANISM: Artificial sequence
<220> FEATURE:
<223> OTHER INFORMATION: Synthesized

<400> SEQUENCE: 12

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
```

```
            20                  25                  30
Tyr Met Lys Trp Val Lys Gln Ala Pro Gly Gln Gly Leu Glu Trp Ile
            35                  40                  45

Gly Asp Ile Ile Pro Ser Asn Gly Ala Thr Phe Tyr Asn Gln Lys Phe
 50                  55                  60

Lys Gly Lys Ala Thr Leu Thr Val Asp Arg Ser Ile Ser Thr Ala Tyr
 65                  70                  75                  80

Met His Leu Asn Arg Leu Arg Ser Asp Thr Ala Val Tyr Tyr Cys
                 85                  90                  95

Thr Arg Ser His Leu Leu Arg Ala Ser Trp Phe Ala Tyr Trp Gly Gln
            100                 105                 110

Gly Thr Leu Val Thr Val Ser Ser
            115                 120

<210> SEQ ID NO 13
<211> LENGTH: 114
<212> TYPE: PRT
<213> ORGANISM: Artificial sequence
<220> FEATURE:
<223> OTHER INFORMATION: Synthesized

<400> SEQUENCE: 13

Asp Phe Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
            100                 105                 110

Lys Arg

<210> SEQ ID NO 14
<211> LENGTH: 112
<212> TYPE: PRT
<213> ORGANISM: Artificial sequence
<220> FEATURE:
<223> OTHER INFORMATION: Synthesized

<400> SEQUENCE: 14

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
```

85                  90                  95

Glu Val Pro Trp Thr Phe Gly Gln Gly Thr Lys Val Glu Ile Lys Arg
                100                 105                 110

<210> SEQ ID NO 15
<211> LENGTH: 118
<212> TYPE: PRT
<213> ORGANISM: Artificial sequence
<220> FEATURE:
<223> OTHER INFORMATION: Synthesized

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser
            115

<210> SEQ ID NO 16
<211> LENGTH: 107
<212> TYPE: PRT
<213> ORGANISM: Artificial sequence
<220> FEATURE:
<223> OTHER INFORMATION: Synthesized

<400> SEQUENCE: 16

Gln Ile Val Leu Ser Gln Ser Pro Ala Thr Leu Ser Leu Ser Pro Gly
1               5                   10                  15

Glu Arg Ala Thr Met Ser Cys Arg Ala Ser Ser Ser Val Ser His Met
                20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95

Phe Gly Gly Gly Thr Lys Val Glu Ile Lys Arg
                100                 105

<210> SEQ ID NO 17
<211> LENGTH: 118
<212> TYPE: PRT
<213> ORGANISM: Artificial sequence
<220> FEATURE:
<223> OTHER INFORMATION: Synthesized

<400> SEQUENCE: 17

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Asp Leu Lys Trp Met
        35                  40                  45

Gly Trp Ile Asn Thr Tyr Ser Gly Glu Pro Arg Tyr Ala Asp Asp Phe
    50                  55                  60

Lys Gly Arg Phe Val Phe Ser Leu Asp Lys Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
            100                 105                 110

Thr Val Thr Val Ser Ser
            115

<210> SEQ ID NO 18
<211> LENGTH: 120
<212> TYPE: PRT
<213> ORGANISM: Artificial sequence
<220> FEATURE:
<223> OTHER INFORMATION: Synthesized

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120

<210> SEQ ID NO 19
<211> LENGTH: 113
<212> TYPE: PRT
<213> ORGANISM: Artificial sequence
<220> FEATURE:
<223> OTHER INFORMATION: Synthesized

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Pro Leu Ile Tyr Lys Ile Ser Thr Arg Phe Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gly Gly Thr Lys Val Glu Ile Lys
                100                 105                 110

Arg

<210> SEQ ID NO 20
<211> LENGTH: 56
<212> TYPE: PRT
<213> ORGANISM: Artificial sequence
<220> FEATURE:
<223> OTHER INFORMATION: Synthesized

<400> SEQUENCE: 20

Leu Glu Ile Arg Ala Ala Phe Leu Arg Gln Arg Asn Thr Ala Leu Arg
 1               5                  10                  15

Thr Glu Val Ala Glu Leu Glu Gln Glu Val Gln Arg Leu Glu Asn Glu
                20                  25                  30

Val Ser Gln Tyr Glu Thr Arg Tyr Ser Gly Gly Gly Gly Pro Leu
                35                  40                  45

Gly Val Arg Gly Gly Gly Gly Ser
     50                  55

<210> SEQ ID NO 21
<211> LENGTH: 40
<212> TYPE: PRT
<213> ORGANISM: Artificial sequence
<220> FEATURE:
<223> OTHER INFORMATION: Synthesized

<400> SEQUENCE: 21

Leu Glu Ile Arg Ala Ala Phe Leu Arg Gln Arg Asn Thr Ala Leu Arg
 1               5                  10                  15

Thr Glu Val Ala Glu Leu Glu Gln Glu Val Gln Arg Leu Glu Asn Glu
                20                  25                  30

Val Ser Gln Tyr Glu Thr Arg Tyr
                35                  40

<210> SEQ ID NO 22
<211> LENGTH: 6
<212> TYPE: PRT
<213> ORGANISM: Artificial sequence
<220> FEATURE:
<223> OTHER INFORMATION: Synthesized

<400> SEQUENCE: 22

Ser Gly Gly Gly Gly Gly
 1               5

<210> SEQ ID NO 23
<211> LENGTH: 5
<212> TYPE: PRT
<213> ORGANISM: Artificial sequence
<220> FEATURE:
<223> OTHER INFORMATION: Synthesized

<400> SEQUENCE: 23

Pro Leu Gly Val Arg
 1               5
```

<210> SEQ ID NO 24
<211> LENGTH: 5
<212> TYPE: PRT
<213> ORGANISM: Artificial sequence
<220> FEATURE:
<223> OTHER INFORMATION: Synthesized

<400> SEQUENCE: 24

Gly Gly Gly Gly Ser
1               5

<210> SEQ ID NO 25
<211> LENGTH: 56
<212> TYPE: PRT
<213> ORGANISM: Artificial sequence
<220> FEATURE:
<223> OTHER INFORMATION: Synthesized

<400> SEQUENCE: 25

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Ala Arg Asn Arg
            20                  25                  30

Val Ser Gln Tyr Arg Thr Arg Tyr Ser Gly Gly Gly Gly Pro Leu
        35                  40                  45

Gly Val Arg Gly Gly Gly Gly Ser
    50                  55

<210> SEQ ID NO 26
<211> LENGTH: 40
<212> TYPE: PRT
<213> ORGANISM: Artificial sequence
<220> FEATURE:
<223> OTHER INFORMATION: Synthesized

<400> SEQUENCE: 26

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Ala Arg Asn Arg
            20                  25                  30

Val Ser Gln Tyr Arg Thr Arg Tyr
        35                  40

<210> SEQ ID NO 27
<211> LENGTH: 56
<212> TYPE: PRT
<213> ORGANISM: Artificial sequence
<220> FEATURE:
<223> OTHER INFORMATION: Synthesized

<400> SEQUENCE: 27

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Ser Gly Gly Gly Gly Pro Leu
        35                  40                  45

Gly Val Arg Gly Gly Gly Gly Ser
    50                  55

<210> SEQ ID NO 28

<211> LENGTH: 40
<212> TYPE: PRT
<213> ORGANISM: Artificial sequence
<220> FEATURE:
<223> OTHER INFORMATION: Synthesized

<400> SEQUENCE: 28

```
Leu Glu Ile Glu Ala Ala Phe Leu Glu Gln Glu Asn Thr Ala Leu Glu
1               5                   10                  15
Thr Glu Val Ala Glu Leu Glu Gln Glu Val Gln Arg Leu Glu Asn Ile
            20                  25                  30
Val Ser Gln Tyr Glu Thr Arg Tyr
        35                  40
```

<210> SEQ ID NO 29
<211> LENGTH: 56
<212> TYPE: PRT
<213> ORGANISM: Artificial sequence
<220> FEATURE:
<223> OTHER INFORMATION: Synthesized

<400> SEQUENCE: 29

```
Leu Glu Ile Arg Ala Ala Phe Leu Arg Arg Arg Asn Thr Ala Leu Arg
1               5                   10                  15
Thr Arg Val Ala Glu Leu Arg Gln Arg Val Gln Arg Leu Arg Asn Ile
            20                  25                  30
Val Ser Gln Tyr Glu Thr Arg Tyr Ser Gly Gly Gly Gly Pro Leu
        35                  40                  45
Gly Val Arg Gly Gly Gly Gly Ser
    50                  55
```

<210> SEQ ID NO 30
<211> LENGTH: 40
<212> TYPE: PRT
<213> ORGANISM: Artificial sequence
<220> FEATURE:
<223> OTHER INFORMATION: Synthesized

<400> SEQUENCE: 30

```
Leu Glu Ile Arg Ala Ala Phe Leu Arg Arg Arg Asn Thr Ala Leu Arg
1               5                   10                  15
Thr Arg Val Ala Glu Leu Arg Gln Arg Val Gln Arg Leu Arg Asn Ile
            20                  25                  30
Val Ser Gln Tyr Glu Thr Arg Tyr
        35                  40
```

<210> SEQ ID NO 31
<211> LENGTH: 48
<212> TYPE: PRT
<213> ORGANISM: Artificial sequence
<220> FEATURE:
<223> OTHER INFORMATION: Synthesized

<400> SEQUENCE: 31

```
Gln Gly Ala Ser Thr Thr Val Ala Gln Leu Glu Glu Lys Val Lys Thr
1               5                   10                  15
Leu Arg Ala Glu Asn Tyr Glu Leu Lys Ser Glu Val Gln Arg Leu Glu
            20                  25                  30
Glu Gln Val Ala Gln Leu Gly Ser Ile Pro Val Ser Leu Arg Ser Gly
        35                  40                  45
```

<210> SEQ ID NO 32

```
<211> LENGTH: 38
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: N-terminal Gln is optional

<400> SEQUENCE: 32

Gln Gly Ala Ser Thr Thr Val Ala Gln Leu Glu Glu Lys Val Lys Thr
1               5                   10                  15

Leu Arg Ala Glu Asn Tyr Glu Leu Lys Ser Glu Val Gln Arg Leu Glu
            20                  25                  30

Glu Gln Val Ala Gln Leu
        35

<210> SEQ ID NO 33
<211> LENGTH: 6
<212> TYPE: PRT
<213> ORGANISM: Artificial sequence
<220> FEATURE:
<223> OTHER INFORMATION: Synthesized

<400> SEQUENCE: 33

Ile Pro Val Ser Leu Arg
1               5

<210> SEQ ID NO 34
<211> LENGTH: 48
<212> TYPE: PRT
<213> ORGANISM: Artificial sequence
<220> FEATURE:
<223> OTHER INFORMATION: Synthesized

<400> SEQUENCE: 34

Gln Gly Ala Ser Thr Ser Val Asp Glu Leu Gln Ala Glu Val Asp Gln
1               5                   10                  15

Leu Glu Asp Glu Asn Tyr Ala Leu Lys Thr Lys Val Ala Gln Leu Arg
            20                  25                  30

Lys Lys Val Glu Lys Leu Gly Ser Ile Pro Val Ser Leu Arg Ser Gly
        35                  40                  45

<210> SEQ ID NO 35
<211> LENGTH: 38
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: N-terminal Gln is optional

<400> SEQUENCE: 35

Gln Gly Ala Ser Thr Ser Val Asp Glu Leu Gln Ala Glu Val Asp Gln
1               5                   10                  15

Leu Glu Asp Glu Asn Tyr Ala Leu Lys Thr Lys Val Ala Gln Leu Arg
            20                  25                  30

Lys Lys Val Glu Lys Leu
        35

<210> SEQ ID NO 36
<211> LENGTH: 61
```

```
<212> TYPE: PRT
<213> ORGANISM: Artificial sequence
<220> FEATURE:
<223> OTHER INFORMATION: Synthesized

<400> SEQUENCE: 36

Glu Ala Cys Gly Ala Leu Glu Ile Arg Ala Ala Phe Leu Arg Gln Arg
1               5                   10                  15

Asn Thr Ala Leu Arg Thr Glu Val Ala Glu Leu Glu Gln Glu Val Gln
            20                  25                  30

Arg Leu Glu Asn Glu Val Ser Gln Tyr Glu Thr Arg Tyr Ser Gly Gly
        35                  40                  45

Gly Gly Gly Pro Leu Gly Val Arg Gly Gly Gly Ser
        50                  55                  60

<210> SEQ ID NO 37
<211> LENGTH: 45
<212> TYPE: PRT
<213> ORGANISM: Artificial sequence
<220> FEATURE:
<223> OTHER INFORMATION: Synthesized

<400> SEQUENCE: 37

Glu Ala Cys Gly Ala Leu Glu Ile Arg Ala Ala Phe Leu Arg Gln Arg
1               5                   10                  15

Asn Thr Ala Leu Arg Thr Glu Val Ala Glu Leu Glu Gln Glu Val Gln
            20                  25                  30

Arg Leu Glu Asn Glu Val Ser Gln Tyr Glu Thr Arg Tyr
        35                  40                  45

<210> SEQ ID NO 38
<211> LENGTH: 61
<212> TYPE: PRT
<213> ORGANISM: Artificial sequence
<220> FEATURE:
<223> OTHER INFORMATION: Synthesized

<400> SEQUENCE: 38

Glu Ala Cys Gly Ala Leu Glu Ile Glu Ala Ala Phe Leu Glu Arg Glu
1               5                   10                  15

Asn Thr Ala Leu Glu Thr Arg Val Ala Glu Leu Arg Gln Arg Val Gln
            20                  25                  30

Arg Ala Arg Asn Arg Val Ser Gln Tyr Arg Thr Arg Tyr Ser Gly Gly
        35                  40                  45

Gly Gly Gly Pro Leu Gly Val Arg Gly Gly Gly Ser
        50                  55                  60

<210> SEQ ID NO 39
<211> LENGTH: 45
<212> TYPE: PRT
<213> ORGANISM: Artificial sequence
<220> FEATURE:
<223> OTHER INFORMATION: Synthesized

<400> SEQUENCE: 39

Glu Ala Cys Gly Ala Leu Glu Ile Glu Ala Ala Phe Leu Glu Arg Glu
1               5                   10                  15

Asn Thr Ala Leu Glu Thr Arg Val Ala Glu Leu Arg Gln Arg Val Gln
            20                  25                  30

Arg Ala Arg Asn Arg Val Ser Gln Tyr Arg Thr Arg Tyr
        35                  40                  45
```

<210> SEQ ID NO 40
<211> LENGTH: 61
<212> TYPE: PRT
<213> ORGANISM: Artificial sequence
<220> FEATURE:
<223> OTHER INFORMATION: Synthesized

<400> SEQUENCE: 40

Glu Ala Cys Gly Ala Leu Glu Ile Glu Ala Ala Phe Leu Glu Gln Glu
1               5                   10                  15

Asn Thr Ala Leu Glu Thr Glu Val Ala Glu Leu Glu Gln Glu Val Gln
            20                  25                  30

Arg Leu Glu Asn Ile Val Ser Gln Tyr Glu Thr Arg Tyr Ser Gly Gly
        35                  40                  45

Gly Gly Gly Pro Leu Gly Val Arg Gly Gly Gly Ser
    50                  55                  60

<210> SEQ ID NO 41
<211> LENGTH: 45
<212> TYPE: PRT
<213> ORGANISM: Artificial sequence
<220> FEATURE:
<223> OTHER INFORMATION: Synthesized

<400> SEQUENCE: 41

Glu Ala Cys Gly Ala Leu Glu Ile Glu Ala Ala Phe Leu Glu Gln Glu
1               5                   10                  15

Asn Thr Ala Leu Glu Thr Glu Val Ala Glu Leu Glu Gln Glu Val Gln
            20                  25                  30

Arg Leu Glu Asn Ile Val Ser Gln Tyr Glu Thr Arg Tyr
        35                  40                  45

<210> SEQ ID NO 42
<211> LENGTH: 61
<212> TYPE: PRT
<213> ORGANISM: Artificial sequence
<220> FEATURE:
<223> OTHER INFORMATION: Synthesized

<400> SEQUENCE: 42

Glu Ala Cys Gly Ala Leu Glu Ile Arg Ala Ala Phe Leu Arg Arg Arg
1               5                   10                  15

Asn Thr Ala Leu Arg Thr Arg Val Ala Glu Leu Arg Gln Arg Val Gln
            20                  25                  30

Arg Leu Arg Asn Ile Val Ser Gln Tyr Glu Thr Arg Tyr Ser Gly Gly
        35                  40                  45

Gly Gly Gly Pro Leu Gly Val Arg Gly Gly Gly Ser
    50                  55                  60

<210> SEQ ID NO 43
<211> LENGTH: 45
<212> TYPE: PRT
<213> ORGANISM: Artificial sequence
<220> FEATURE:
<223> OTHER INFORMATION: Synthesized

<400> SEQUENCE: 43

Glu Ala Cys Gly Ala Leu Glu Ile Arg Ala Ala Phe Leu Arg Arg Arg
1               5                   10                  15

Asn Thr Ala Leu Arg Thr Arg Val Ala Glu Leu Arg Gln Arg Val Gln
            20                  25                  30

Arg Leu Arg Asn Ile Val Ser Gln Tyr Glu Thr Arg Tyr
        35                  40                  45

<210> SEQ ID NO 44
<211> LENGTH: 50
<212> TYPE: PRT
<213> ORGANISM: Artificial sequence
<220> FEATURE:
<223> OTHER INFORMATION: Synthesized

<400> SEQUENCE: 44

Glu Ala Cys Gly Ala Ser Thr Thr Val Ala Gln Leu Glu Glu Lys Val
1               5                   10                  15

Lys Thr Leu Arg Ala Glu Asn Tyr Glu Leu Lys Ser Glu Val Gln Arg
            20                  25                  30

Leu Glu Glu Gln Val Ala Gln Leu Gly Ser Ile Pro Val Ser Leu Arg
        35                  40                  45

Ser Gly
    50

<210> SEQ ID NO 45
<211> LENGTH: 40
<212> TYPE: PRT
<213> ORGANISM: Artificial sequence
<220> FEATURE:
<223> OTHER INFORMATION: Synthesized

<400> SEQUENCE: 45

Glu Ala Cys Gly Ala Ser Thr Thr Val Ala Gln Leu Glu Glu Lys Val
1               5                   10                  15

Lys Thr Leu Arg Ala Glu Asn Tyr Glu Leu Lys Ser Glu Val Gln Arg
            20                  25                  30

Leu Glu Glu Gln Val Ala Gln Leu
        35                  40

<210> SEQ ID NO 46
<211> LENGTH: 50
<212> TYPE: PRT
<213> ORGANISM: Artificial sequence
<220> FEATURE:
<223> OTHER INFORMATION: Synthesized

<400> SEQUENCE: 46

Glu Ala Cys Gly Ala Ser Thr Ser Val Asp Glu Leu Gln Ala Glu Val
1               5                   10                  15

Asp Gln Leu Glu Asp Glu Asn Tyr Ala Leu Lys Thr Lys Val Ala Gln
            20                  25                  30

Leu Arg Lys Lys Val Glu Lys Leu Gly Ser Ile Pro Val Ser Leu Arg
        35                  40                  45

Ser Gly
    50

<210> SEQ ID NO 47
<211> LENGTH: 40
<212> TYPE: PRT
<213> ORGANISM: Artificial sequence
<220> FEATURE:
<223> OTHER INFORMATION: Synthesized

<400> SEQUENCE: 47

Glu Ala Cys Gly Ala Ser Thr Ser Val Asp Glu Leu Gln Ala Glu Val
1               5                   10                  15

Asp Gln Leu Glu Asp Glu Asn Tyr Ala Leu Lys Thr Lys Val Ala Gln
            20                  25                  30

Leu Arg Lys Lys Val Glu Lys Leu
        35                  40

<210> SEQ ID NO 48
<211> LENGTH: 10
<212> TYPE: PRT
<213> ORGANISM: Artificial sequence
<220> FEATURE:
<223> OTHER INFORMATION: Synthesized

<400> SEQUENCE: 48

Gly Ser Ile Pro Val Ser Leu Arg Ser Gly
1               5                   10

<210> SEQ ID NO 49
<211> LENGTH: 5
<212> TYPE: PRT
<213> ORGANISM: Artificial sequence
<220> FEATURE:
<223> OTHER INFORMATION: Synthesized

<400> SEQUENCE: 49

Gly Ser Gly Gly Ser
1               5

<210> SEQ ID NO 50
<211> LENGTH: 4
<212> TYPE: PRT
<213> ORGANISM: Artificial sequence
<220> FEATURE:
<223> OTHER INFORMATION: Synthesized

<400> SEQUENCE: 50

Gly Gly Gly Ser
1

<210> SEQ ID NO 51
<211> LENGTH: 12
<212> TYPE: PRT
<213> ORGANISM: Artificial sequence
<220> FEATURE:
<223> OTHER INFORMATION: Synthesized

<400> SEQUENCE: 51

Ser Gly Gly Gly Gly Gly Gly Gly Gly Gly Gly Ser
1               5                   10

<210> SEQ ID NO 52
<211> LENGTH: 4
<212> TYPE: PRT
<213> ORGANISM: Artificial sequence
<220> FEATURE:
<223> OTHER INFORMATION: Synthesized

<400> SEQUENCE: 52

Gly Gly Ala Ala
1

<210> SEQ ID NO 53
<211> LENGTH: 5
<212> TYPE: PRT
<213> ORGANISM: Artificial sequence
<220> FEATURE:
<223> OTHER INFORMATION: Synthesized

```
<400> SEQUENCE: 53

Leu Ala Ala Ala Ala
1               5

<210> SEQ ID NO 54
<211> LENGTH: 4
<212> TYPE: PRT
<213> ORGANISM: Artificial sequence
<220> FEATURE:
<223> OTHER INFORMATION: Synthesized

<400> SEQUENCE: 54

Gly Gly Ser Gly
1

<210> SEQ ID NO 55
<211> LENGTH: 5
<212> TYPE: PRT
<213> ORGANISM: Artificial sequence
<220> FEATURE:
<223> OTHER INFORMATION: Synthesized

<400> SEQUENCE: 55

Gly Gly Ser Gly Gly
1               5

<210> SEQ ID NO 56
<211> LENGTH: 5
<212> TYPE: PRT
<213> ORGANISM: Artificial sequence
<220> FEATURE:
<223> OTHER INFORMATION: Synthesized

<400> SEQUENCE: 56

Gly Ser Gly Ser Gly
1               5

<210> SEQ ID NO 57
<211> LENGTH: 5
<212> TYPE: PRT
<213> ORGANISM: Artificial sequence
<220> FEATURE:
<223> OTHER INFORMATION: Synthesized

<400> SEQUENCE: 57

Gly Ser Gly Gly Gly
1               5

<210> SEQ ID NO 58
<211> LENGTH: 5
<212> TYPE: PRT
<213> ORGANISM: Artificial sequence
<220> FEATURE:
<223> OTHER INFORMATION: Synthesized

<400> SEQUENCE: 58

Gly Gly Gly Ser Gly
1               5

<210> SEQ ID NO 59
<211> LENGTH: 5
<212> TYPE: PRT
<213> ORGANISM: Artificial sequence
<220> FEATURE:
<223> OTHER INFORMATION: Synthesized

<400> SEQUENCE: 59
```

-continued

```
Gly Ser Ser Ser Gly
1               5

<210> SEQ ID NO 60
<211> LENGTH: 6
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (4)..(6)
<223> OTHER INFORMATION: Xaa can be any naturally occurring amino acid

<400> SEQUENCE: 60

Pro Leu Gly Xaa Xaa Xaa
1               5

<210> SEQ ID NO 61
<211> LENGTH: 8
<212> TYPE: PRT
<213> ORGANISM: Artificial sequence
<220> FEATURE:
<223> OTHER INFORMATION: Synthesized

<400> SEQUENCE: 61

Leu Ser Gly Arg Ser Asp Asn His
1               5

<210> SEQ ID NO 62
<211> LENGTH: 6
<212> TYPE: PRT
<213> ORGANISM: Artificial sequence
<220> FEATURE:
<223> OTHER INFORMATION: Synthesized

<400> SEQUENCE: 62

Gly Pro Leu Gly Val Arg
1               5

<210> SEQ ID NO 63
<211> LENGTH: 4
<212> TYPE: PRT
<213> ORGANISM: Artificial sequence
<220> FEATURE:
<223> OTHER INFORMATION: Synthesized

<400> SEQUENCE: 63

Gly Phe Leu Gly
1

<210> SEQ ID NO 64
<211> LENGTH: 47
<212> TYPE: PRT
<213> ORGANISM: Artificial sequence
<220> FEATURE:
<223> OTHER INFORMATION: Synthesized

<400> SEQUENCE: 64

Gly Ala Ser Thr Ser Val Asp Glu Leu Gln Ala Glu Val Asp Gln Leu
1               5                   10                  15

Glu Asp Glu Asn Tyr Ala Leu Lys Thr Lys Val Ala Gln Leu Arg Lys
            20                  25                  30

Lys Val Glu Lys Leu Gly Ser Ile Pro Val Ser Leu Arg Ser Gly
        35                  40                  45
```

```
<210> SEQ ID NO 65
<211> LENGTH: 47
<212> TYPE: PRT
<213> ORGANISM: Artificial sequence
<220> FEATURE:
<223> OTHER INFORMATION: Synthesized

<400> SEQUENCE: 65

Gly Ala Ser Thr Thr Val Ala Gln Leu Glu Glu Lys Val Lys Thr Leu
1               5                   10                  15

Arg Ala Glu Asn Tyr Glu Leu Lys Ser Glu Val Gln Arg Leu Glu Glu
            20                  25                  30

Gln Val Ala Gln Leu Gly Ser Ile Pro Val Ser Leu Arg Ser Gly
        35                  40                  45

<210> SEQ ID NO 66
<211> LENGTH: 39
<212> TYPE: PRT
<213> ORGANISM: Artificial sequence
<220> FEATURE:
<223> OTHER INFORMATION: Synthesized

<400> SEQUENCE: 66

Gly Ala Ser Thr Ser Val Asp Glu Leu Gln Ala Glu Val Asp Gln Leu
1               5                   10                  15

Gln Asp Glu Asn Tyr Ala Leu Lys Thr Lys Val Ala Gln Leu Arg Lys
            20                  25                  30

Lys Val Glu Lys Leu Ser Glu
        35

<210> SEQ ID NO 67
<211> LENGTH: 38
<212> TYPE: PRT
<213> ORGANISM: Artificial sequence
<220> FEATURE:
<223> OTHER INFORMATION: Synthesized

<400> SEQUENCE: 67

Gly Ala Ser Thr Thr Val Ala Gln Leu Arg Glu Arg Val Lys Thr Leu
1               5                   10                  15

Arg Ala Gln Asn Tyr Glu Leu Glu Ser Glu Val Gln Arg Leu Arg Glu
            20                  25                  30

Gln Val Ala Gln Leu Ala
        35

<210> SEQ ID NO 68
<211> LENGTH: 42
<212> TYPE: PRT
<213> ORGANISM: Artificial sequence
<220> FEATURE:
<223> OTHER INFORMATION: Synthesized

<400> SEQUENCE: 68

Glu Ala Cys Gly Ala Ser Thr Ser Val Asp Glu Leu Gln Ala Glu Val
1               5                   10                  15

Asp Gln Leu Gln Asp Glu Asn Tyr Ala Leu Lys Thr Lys Val Ala Gln
            20                  25                  30

Leu Arg Lys Lys Val Glu Lys Leu Ser Glu
        35                  40

<210> SEQ ID NO 69
<211> LENGTH: 41
```

<212> TYPE: PRT
<213> ORGANISM: Artificial sequence
<220> FEATURE:
<223> OTHER INFORMATION: Synthesized

<400> SEQUENCE: 69

Glu Ala Cys Gly Ala Ser Thr Thr Val Ala Gln Leu Arg Glu Arg Val
1               5                   10                  15

Lys Thr Leu Arg Ala Gln Asn Tyr Glu Leu Glu Ser Glu Val Gln Arg
            20                  25                  30

Leu Arg Glu Gln Val Ala Gln Leu Ala
        35                  40

<210> SEQ ID NO 70
<211> LENGTH: 42
<212> TYPE: PRT
<213> ORGANISM: Artificial sequence
<220> FEATURE:
<223> OTHER INFORMATION: Synthesized

<400> SEQUENCE: 70

Ala Gly Leu Thr Asp Thr Leu Gln Ala Glu Thr Asp Gln Leu Glu Asp
1               5                   10                  15

Lys Lys Ser Ala Leu Gln Thr Glu Ile Ala Asn Leu Leu Lys Glu Lys
            20                  25                  30

Glu Lys Leu Glu Phe Ile Leu Ala Ala His
        35                  40

<210> SEQ ID NO 71
<211> LENGTH: 42
<212> TYPE: PRT
<213> ORGANISM: Artificial sequence
<220> FEATURE:
<223> OTHER INFORMATION: Synthesized

<400> SEQUENCE: 71

Ala Gly Arg Ile Ala Arg Leu Glu Glu Lys Val Lys Thr Leu Lys Ala
1               5                   10                  15

Gln Asn Ser Glu Leu Ala Ser Thr Ala Asn Met Leu Arg Glu Gln Val
            20                  25                  30

Ala Gln Leu Lys Gln Lys Val Met Asn Tyr
        35                  40

<210> SEQ ID NO 72
<211> LENGTH: 46
<212> TYPE: PRT
<213> ORGANISM: Artificial sequence
<220> FEATURE:
<223> OTHER INFORMATION: Synthesized

<400> SEQUENCE: 72

Glu Ala Cys Gly Ala Gly Leu Thr Asp Thr Leu Gln Ala Glu Thr Asp
1               5                   10                  15

Gln Leu Glu Asp Lys Lys Ser Ala Leu Gln Thr Glu Ile Ala Asn Leu
            20                  25                  30

Leu Lys Glu Lys Glu Lys Leu Glu Phe Ile Leu Ala Ala His
        35                  40                  45

<210> SEQ ID NO 73
<211> LENGTH: 46
<212> TYPE: PRT
<213> ORGANISM: Artificial sequence
<220> FEATURE:

<223> OTHER INFORMATION: Synthesized

<400> SEQUENCE: 73

Glu Ala Cys Gly Ala Gly Arg Ile Ala Arg Leu Glu Glu Lys Val Lys
1               5                   10                  15

Thr Leu Lys Ala Gln Asn Ser Glu Leu Ala Ser Thr Ala Asn Met Leu
            20                  25                  30

Arg Glu Gln Val Ala Gln Leu Lys Gln Lys Val Met Asn Tyr
        35                  40                  45

<210> SEQ ID NO 74
<211> LENGTH: 29
<212> TYPE: PRT
<213> ORGANISM: Artificial sequence
<220> FEATURE:
<223> OTHER INFORMATION: Synthesized

<400> SEQUENCE: 74

Gly Lys Ile Ala Ala Leu Lys Gln Lys Ile Ala Ala Leu Lys Tyr Lys
1               5                   10                  15

Asn Ala Ala Leu Lys Lys Lys Ile Ala Ala Leu Lys Gln
            20                  25

<210> SEQ ID NO 75
<211> LENGTH: 29
<212> TYPE: PRT
<213> ORGANISM: Artificial sequence
<220> FEATURE:
<223> OTHER INFORMATION: Synthesized

<400> SEQUENCE: 75

Gly Glu Ile Ala Ala Leu Glu Gln Glu Ile Ala Ala Leu Glu Lys Glu
1               5                   10                  15

Asn Ala Ala Leu Glu Trp Glu Ile Ala Ala Leu Glu Gln
            20                  25

<210> SEQ ID NO 76
<211> LENGTH: 34
<212> TYPE: PRT
<213> ORGANISM: Artificial sequence
<220> FEATURE:
<223> OTHER INFORMATION: Synthesized

<400> SEQUENCE: 76

Glu Ala Cys Gly Ala Gly Lys Ile Ala Ala Leu Lys Gln Lys Ile Ala
1               5                   10                  15

Ala Leu Lys Tyr Lys Asn Ala Ala Leu Lys Lys Lys Ile Ala Ala Leu
            20                  25                  30

Lys Gln

<210> SEQ ID NO 77
<211> LENGTH: 34
<212> TYPE: PRT
<213> ORGANISM: Artificial sequence
<220> FEATURE:
<223> OTHER INFORMATION: Synthesized

<400> SEQUENCE: 77

Glu Ala Cys Gly Ala Gly Glu Ile Ala Ala Leu Glu Gln Glu Ile Ala
1               5                   10                  15

Ala Leu Glu Lys Glu Asn Ala Ala Leu Glu Trp Glu Ile Ala Ala Leu
            20                  25                  30

Glu Gln

<210> SEQ ID NO 78
<211> LENGTH: 8
<212> TYPE: PRT
<213> ORGANISM: Artificial sequence
<220> FEATURE:
<223> OTHER INFORMATION: Synthesized

<400> SEQUENCE: 78

Val Pro Met Ser Met Arg Gly Gly
1               5

<210> SEQ ID NO 79
<211> LENGTH: 8
<212> TYPE: PRT
<213> ORGANISM: Artificial sequence
<220> FEATURE:
<223> OTHER INFORMATION: Synthesized

<400> SEQUENCE: 79

Arg Pro Phe Ser Met Ile Met Gly
1               5

<210> SEQ ID NO 80
<211> LENGTH: 8
<212> TYPE: PRT
<213> ORGANISM: Artificial sequence
<220> FEATURE:
<223> OTHER INFORMATION: Synthesized

<400> SEQUENCE: 80

Ile Pro Glu Ser Leu Arg Ala Gly
1               5

<210> SEQ ID NO 81
<211> LENGTH: 8
<212> TYPE: PRT
<213> ORGANISM: Artificial sequence
<220> FEATURE:
<223> OTHER INFORMATION: Synthesized

<400> SEQUENCE: 81

Val Pro Leu Ser Leu Thr Met Gly
1               5

<210> SEQ ID NO 82
<211> LENGTH: 6
<212> TYPE: PRT
<213> ORGANISM: Artificial sequence
<220> FEATURE:
<223> OTHER INFORMATION: Synthesized

<400> SEQUENCE: 82

Pro Leu Gly Leu Ala Gly
1               5

<210> SEQ ID NO 83
<211> LENGTH: 6
<212> TYPE: PRT
<213> ORGANISM: Artificial sequence
<220> FEATURE:
<223> OTHER INFORMATION: Synthesized

<400> SEQUENCE: 83

Leu Ala Leu Gly Pro Gly
1               5

-continued

```
<210> SEQ ID NO 84
<211> LENGTH: 5
<212> TYPE: PRT
<213> ORGANISM: Artificial sequence
<220> FEATURE:
<223> OTHER INFORMATION: Synthesized

<400> SEQUENCE: 84

Tyr Gly Arg Ala Ala
1               5
```

US 11,230,610 B2

BIVALENT ANTIBODIES MASKED BY COILED COILS

CROSS REFERENCE TO RELATED APPLICATIONS

This application is a national stage entry of PCT/US2017/065471 filed Dec. 8, 2017, which claims the benefit of U.S. 62/432,472, filed Dec. 9, 2016, which is incorporated by reference in its entirety for all purposes.

REFERENCE TO A SEQUENCE LISTING

This application includes an electronic sequence listing in a file named 531353SEQLIST.TXT, created on May 1, 2019, and containing 51,346 bytes, which is incorporated by reference.

BACKGROUND

Current antibody-based therapeutics may have less than optimal selectivity for the intended target. Although monoclonal antibodies are typically specific for binding to their intended targets, most target molecules are not specific to the disease site and may be present in cells or tissues other than the disease site.

Several approaches have been described for overcoming these off-target effects by engineering antibodies to have a cleavable linker attached to an inhibitory or masking domain that inhibits antibody binding (see, e.g., WO2003/068934, WO2004/009638, WO 2009/025846, WO2101/081173 and WO2014103973). The linker can be designed to be cleaved by enzymes that are specific to certain tissues or pathologies, thus enabling the antibody to be preferentially activated in desired locations. Masking moieties can act by binding directly to the binding site of an antibody or can act indirectly via steric hindrance. Various masking moieties, linkers, protease sites and formats of assembly have been proposed. The extent of masking may vary between different formats as may the compatibility of masking moieties with expression, purification, conjugation, or pharmacokinetics of antibodies.

SUMMARY OF THE CLAIMED INVENTION

The invention provides a bivalent antibody comprising two light and heavy chain pairs, wherein the N-termini of the light and heavy chains of at least one of the pairs are linked via linkers comprising a protease cleavage site to coiled-coil forming peptides that associate to form a coiled coil reducing binding affinity of the light-heavy chain pair to a target. Optionally, the light and heavy chains of both of the pairs are linked via linkers comprising a protease cleavage site to coiled-coil forming peptides that associate to form a coiled coil reducing binding affinity of the light-heavy chain pair to a target.

Optionally, the peptides associate without forming a disulfide bridge. Optionally, the bivalent antibody is conjugated to a cytotoxic or cytostatic drug. Optionally, the cytotoxic or cytostatic drug is conjugated via a cysteine residue of the bivalent antibody. Optionally, the two light and heavy chain pairs are the same. Optionally, the two light and heavy chain pairs are different. Optionally, the light chains include a light chain variable region and light chain constant region and the heavy chains include a heavy chain variable region and heavy chain constant region. Optionally, the heavy chain region includes CH1, hinge, CH2 and CH3 regions. Optionally, the two light chains are linked to a first heterologous peptide and the two heavy chains to a second heterologous peptide. Optionally, the protease cleavage site is any of MMP #1 or MMP #2. Optionally, the target is any of CD19, CD30, LIV-1, CD70, or CD74. Optionally, the binding is reduced at least 100-fold. Optionally, the binding is reduced 200-5000, 200-4000 fold or 200-1500 fold. Optionally, cytotoxicity of the conjugate is reduced at least 100-fold. Optionally, cytotoxicity of the conjugate is reduced 200-5000 fold. Optionally, the coiled coil forming peptides are linked to the N-termini of the heavy and light chains in the same orientation. Optionally, the coiled coil forming peptides are linked to the N-termini of the heavy and light chains in opposing orientations. Optionally, multiple copies of the coiled coil forming peptide are linked in tandem to the N-termini of the heavy and light chains.

Optionally a peptide comprising or consisting of the sequence of SEQ ID NO: 44 provides the linker comprising a protease cleavage site and the coiled-coil forming peptide linked to the light chain and a peptide of sequence SEQ ID NO: 47 provides the linker comprising a protease cleavage site and the coiled-coil forming peptide linked to the heavy chain.

In another embodiment, a peptide comprising or consisting of the sequence of SEQ ID NO: 46 provides the linker comprising a protease cleavage site and the coiled-coil forming peptide linked to the heavy chain and a peptide of sequence SEQ ID NO: 47 provides the linker comprising a protease cleavage site and the coiled-coil forming peptide linked to the light chain.

In another embodiment, a peptide comprising or consisting of the sequence of QGASTSVDELQAEVDQLEDE-NYALKTKVAQLRKKVEKLGSIPVSLRSG (SEQ ID NO: 34) provides the linker comprising a protease cleavage site and the coiled-coil forming peptide linked to the heavy chain and a peptide of the sequence of QGASTTVAQLEEKVKTLRAENYELKSEVQRLE-EQVAQLGSIPVSLRSG (SEQ ID NO: 31) provides the linker comprising a protease cleavage site and the coiled-coil forming peptide linked to the light chain.

In another embodiment, a peptide comprising or consisting of the sequence of QGASTSVDELQAEVDQLEDE-NYALKTKVAQLRKKVEKLGSIPVSLRSG (SEQ ID NO: 34) provides the linker comprising a protease cleavage site and the coiled-coil forming peptide linked to the light chain and a peptide of the sequence of QGASTTVAQLEEKVKTLRAENYELKSEVQRLE-EQVAQLGSIPVSLRSG (SEQ ID NO: 31) provides the linker comprising a protease cleavage site and the coiled-coil forming peptide linked to the heavy chain.

In another embodiment, a peptide comprising or consisting of the sequence of GASTSVDELQAEVDQLEDE-NYALKTKVAQLRKKVEKLGSIPVSLRSG (SEQ ID NO: 64) provides the linker comprising a protease cleavage site and the coiled-coil forming peptide linked to the heavy chain and a peptide of the sequence of GASTTVAQLEEKVKTL-RAENYELKSEVQRLEEQVAQLGSIPVSLRSG (SEQ ID NO: 65) provides the linker comprising a protease cleavage site and the coiled-coil forming peptide linked to the light chain.

In another embodiment, a peptide comprising or consisting of the sequence of GASTSVDELQAEVDQLEDE-NYALKTKVAQLRKKVEKLGSIPVSLRSG (SEQ ID NO: 65) provides the linker comprising a protease cleavage site and the coiled-coil forming peptide linked to the light chain and a peptide of the sequence of GASTTVAQLEEKVKTL-RAENYELKSEVQRLEEQVAQLGSIPVSLRSG (SEQ ID NO: 64) provides the linker comprising a protease cleavage site and the coiled-coil forming peptide linked to the heavy chain.

Optionally, the linkers are 1-20, 2-15, 3-12, 4-10, 5, 6, 7, 8, 9 or 10 amino acids in length. A preferred linker has an amino acid sequence comprising or consisting of GSIPVSLRSG (SEQ ID NO: 48). Some linkers comprise an MMP2 protease site.

BRIEF DESCRIPTIONS OF DRAWINGS

FIG. 1A shows examples of coiled coils forming peptides, linkers and protease sites. In M11 CC and M15 CC, SGGGGG (SEQ ID NO: 22) and GGGGS (SEQ ID NO: 24) are linkers. PLGVR (SEQ ID NO: 23) is a protease cleavage site, and the remaining sequences are coiled coil peptides. SEQ ID NO: 20 is a M11 coiled-coil peptide attached to a linker including a protease site (shown as linked to a light chain), and SEQ ID NO: 25 is a M11 coiled peptide attached to a linker including a protease site (shown as linked to a heavy chain). SEQ ID NO: 21 is a M11 coiled coil peptide (shown as linked to a light chain), and SEQ ID NO: 26 is an M11 coiled-coil peptide (shown as linked to a heavy chain). SEQ ID NO: 27 is a M15 CC coiled-coil peptide attached to a linker including a protease site (shown as linked to a light chain), and SEQ ID NO: 29 is a M15 coiled-coil peptide attached to a linker including a protease site (shown as linked to a heavy chain). SEQ ID NO: 28 is a M15 coiled coil peptide (shown as linked to a light chain), and SEQ ID NO: 30 is a M15 coiled-coil peptide (shown as linked to a heavy chain). In VelCC GS and SG are linkers and IPVSLR (SEQ ID NO: 33) is a protease cleavage site and the remaining sequence are coiled coil peptides. SEQ ID NO: 31 is a Vel coiled-coil peptide attached to a linker including a protease site (shown as linked to a light chain), and SEQ ID NO: 34 is Vel coiled peptide attached to a linker including a protease site (shown as linked to a heavy chain). SEQ ID NO: 32 is a Vel coiled coil peptide (shown as linked to a light chain), and SEQ ID NO: 35 is a Vel coiled-coil peptide (shown as linked to a heavy chain). The VEL coiled coil peptides shown in FIG. 1A can be supplemented with an additional N-terminal Q.

FIG. 1B shows examples of coiled coils forming peptides with N-terminal cysteine, linkers and protease sites. In CM11 CC and CM15 CC, SGGGGG (SEQ ID NO: 22) and GGGGS (SEQ ID NO: 24) are linkers. PLGVR (SEQ ID NO: 23) is a protease cleavage site, and the remaining sequences are coiled coil peptides. SEQ ID NO: 36 is a CM11 coiled-coil peptide attached to a linker including a protease site (shown as linked to a light chain), and SEQ ID NO: 38 is a CM11 coiled peptide attached to a linker including a protease site (shown as linked to a heavy chain). SEQ ID NO: 37 is a CM11 coiled coil peptide (shown as linked to a light chain), and SEQ ID NO: 39 is a CM11 coiled-coil peptide (shown as linked to a heavy chain). SEQ ID NO: 40 is a CM15 coiled-coil peptide attached to a linker including a protease site (shown as linked to a light chain), and SEQ ID NO: 42 is CM15 coiled peptide attached to a linker including a protease site (shown as linked to a heavy chain). SEQ ID NO: 41 is a CM15 coiled coil peptide (shown as linked to a light chain), and SEQ ID NO: 43 is a CM15 coiled-coil peptide (shown as linked to a heavy chain). In CVel, GS and SG are linkers and IPVSLR (SEQ ID NO: 33) is a protease cleavage site and the remaining sequences are coiled coil peptides. SEQ ID NO: 44 is a CVel coiled-coil peptide attached to a linker including a protease site (shown as linked to a light chain), and SEQ ID NO: 46 is a CVel coiled peptide attached to a linker including a protease site (shown as linked to a heavy chain). SEQ ID NO: 45 is a CVel coiled coil peptide (shown as linked to a light chain), and SEQ ID NO: 47 is a CVel coiled-coil peptide (shown as linked to a heavy chain).

FIG. 2 shows concentrations of antibodies versus time for various coiled coil masked antibodies incubated in plasma as compared with an hBU12ec control.

FIG. 3 shows a tumor tissue sample contacted by a masked antibody.

Figure 5:
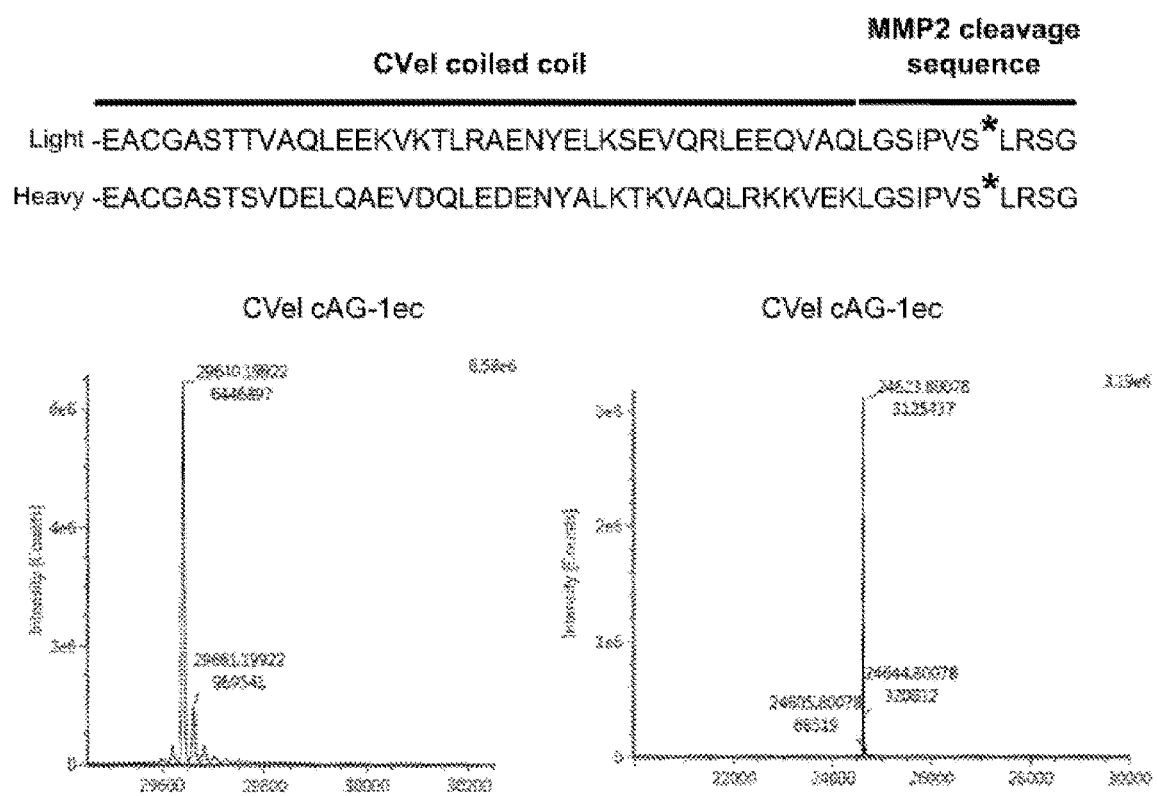

FIG. 5 shows an example of PLRP-MS used to determine cleavage of a peptide sequence. In CVel, GS and SG are linkers and IPVSLR (SEQ ID NO: 33) is a protease cleavage site and the remaining sequence are coiled coil peptides. SEQ ID NO: 44 is a CVel coiled-coil peptide attached to a linker including a protease site (shown as linked to a light chain), and SEQ ID NO: 46 is a CVel coiled peptide attached to a linker including a protease site (shown as linked to a heavy chain). SEQ ID NO: 45 is a CVel coiled coil peptide (shown as linked to a light chain), and SEQ ID NO: 47 is a CVel coiled-coil peptide (shown as linked to a heavy chain).

FIGS. 6A and 6B show in vivo comparison data of hAg-2 with linker CVel or Vel in different tissues. FIG. 6A shows in vivo comparison data of hAg-2 with linker CVel or Vel in tumor, lung, liver, and plasma on day 3 and day 4. FIG. 6B shows in vivo comparison data of hAg-2 with linker Vel-IPV in tumor, lung, and plasma on days 1, 2, and 4.

FIGS. 7A-C show the effects of masking of anti-Ag2 using either CVel or Vel-coiled coil in three different cell lines: HCT116 (FIG. 7A), SW780 (FIG. 7B), and HT1080 (FIG. 7C).

FIGS. 8A-C show comparison unmasked and Vel-masked anti-CD19 antibody-drug conjugates with varying cleavage sequences. FIG. 8A shows unmasked and Vel-masked anti-CD19 ADCs binding to CD19-positive Ramos cells; FIG. 8B shows anti-proliferative activity of anti-CD19 ADCs on CD19-positive Ramos cells; FIG. 8C shows antitumor activity of unmasked and Vel-masked anti-CD19 antibody-drug conjugates in a Ramos xenograft model in NSG mice.

FIGS. 9A-D show the comparison of unmasked and masked anti-mouse CD3 antibody 145-2C11. FIG. 9A shows the binding activity of masked anti-mouse CD3 antibody 145-2C11; FIG. 9B shows the target-mediated drug disposition of unmasked and masked anti-mouse CD3 antibody 145-2C11 in BALB/c mice; FIGS. 9C and D show the mitigation of cytokine release IFN-gamma (FIG. 9C) and IL-2 (FIG. 9D) by anti-CD3 antibody 145-2C11.

FIG. 10 shows the stability of masked Anti-human-Ag2 antibodies bearing different coiled coil domains using intravenous administration to BALB/c mice.

FIGS. 11A-C shows the activities of unmasked and masked anti-mouse Ag2 antibody. FIG. 11A shows a mouse reactive anti-Ag2 antibody masked by the same VEL and IPV sequence used on the human Ag2 antibody; FIG. 11B shows platelets depletion study of masked anti-mouse Ag2 antibody in BALB/c mice; FIG. 11C shows the pharmacokinetics of masked anti-mouse Vel-IPV-Ag2 antibody.

FIGS. 12A-D show the antitumor activity of anti-mouse Ag2 antibody in an A20 lymphoma model. FIG. 12A shows the effect of unmasked and Vel-IPV masked anti-Ag2 antibody on peripheral Ag2(+) cells; FIG. 12B shows the tumor volume change over time after the treatment of unmasked and Vel-IPV masked anti-Ag2 antibody; FIG. 12C shows the binding of unmasked and Vel-IPV masked anti-Ag2 antibody to peripheral cells; and FIG. 12D shows the binding of unmasked and Vel-IPV masked anti-Ag2 antibody to tumor cells.

FIGS. 13A-C show the impact of masking on Anti-Ag2 antibody pharmacokinetics and tolerability. FIG. 13A shows the pharmacokinetics of anti-Ag2 and Vel-IPV-Anti-Ag2 using a generic total antibody (TAb) ELISA; FIG. 13B shows the impacts of masking of anti-Ag2 using Vel-IPV by comparing the depletion of these peripheral Ag2(+) cells; FIG. 13C shows the impacts of masking of anti-Ag2 using Vel-IPV on cytokine production.

FIGS. 14A and 14B show the antitumor activity of anti-Ag2 antibody in L428 xenografts. FIG. 14A shows the tumor volume change after the treatment of Vel-PLGLAG-anti-Ag2 and Vel-LALGPG-anti-Ag2; FIG. 14B shows the L428 cell change after the treatment of Vel-PLGLAG-anti-Ag2 and Vel-LALGPG-anti-Ag2.

DEFINITIONS

An isolated antibody or ADC is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies or ADCs are at least 60%, 70%, 80%, 90%, 95 or 99% w/w pure of interfering proteins and contaminants from production or purification.

Specific binding of an antibody alone or as a component of an ADC to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region is a light chain variable region without the light chain signal peptide. The carboxy-terminal portion of each chain defines a constant region. The heavy chain constant region is primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, antibody fragments compete with the intact antibody from which they were derived for specific binding to the target including separate heavy chains, light chains Fab, Fab', $F(ab')_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$) a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). The term "antibody" includes an antibody by itself (naked antibody) or an antibody conjugated to a cytotoxic or cytostatic drug.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×)

inhibits binding of the reference antibody by at least 50% but preferably 75%, 90% or 99% as measured in a competitive binding assay. Antibodies identified by competition assays (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with sequences maximally aligned.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Antibody sequences are aligned by the Kabat numbering convention such that residues occupying the same numbered position are aligned. After alignment, if a subject sequence a reference sequence, the percentage sequence identity between the subject and reference sequences is the number of positions occupied by the same amino acid in both the subject and reference sequences divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD16+ effector cells through the secretion of membrane pore-forming proteins and proteases, while phagocytosis is mediated by CD32+ and CD64+ effector cells (see *Fundamental Immunology*, 4$^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the protease activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N.Y., 2005, Chapter 2).

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an antibody or ADC is combined.

The phrase "pharmaceutically acceptable salt," refers to pharmaceutically acceptable organic or inorganic salts of an antibody or conjugate thereof or agent administered with an antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. Unless otherwise apparent from the context any of the antibodies or antibody drug conjugates in masked or unmasked form can be provided in the form of pharmaceutically acceptable salt.

Unless otherwise apparent from the context, the term "about" encompasses values within a standard deviation of a stated value.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205, 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having its CDRs, preferably as defined by Kabat, entirely or substantially from a donor antibody and variable region framework sequences and constant regions, if present, entirely or substantially from human antibody sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

A chimeric antibody is an antibody in which the mature variable regions of light and heavy chains of a non-human antibody (e.g., a mouse) are combined with human or nonhuman primate light and heavy chain constant regions. Such antibodies substantially or entirely retain the binding specificity of the mouse antibody, and are about two-thirds human or non-human primate sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

An antibody-drug conjugate (ADC) comprises an antibody conjugated to a drug. A drug is a compound known or suspected to have pharmacological activity, usually cytotoxic or cytostatic activity.

DETAILED DESCRIPTION

I. General

The invention provides antibodies in which variable regions are masked by linkage of the N-termini of variable regions chains to coiled-coil forming peptides. The coiled-coil forming peptides associate with one another to form coiled coils (i.e., the respective peptides each form coils and these coils are coiled around each other). Although an understanding of mechanism is not required for practice of the invention, it is believed the coiled coils sterically inhibit binding of the antibody binding site to its target. The technology can be practiced on all forms of antibodies including bivalent antibodies (i.e., having two binding sites). Non-covalent associations between the coiled coil forming peptides are sufficient to form a stable coiled coils inhibiting binding of the antibody variable region; it is not for example necessary for the coiled-coil forming peptides to be further linked by a disulfide bridge between terminal cysteines of the respective peptides. The presence of non-naturally occurring cysteines is potentially disadvantageous because they can lead to misfolding or misconjugation problems. Masking of antibodies by this format can reduce binding affinities (and cytotoxic activities in the case of ADC's) by over a hundred fold. Antibodies can be masked in this format without significant impairment of expression, purification, conjugation, pharmacokinetics, or binding or other activity on unmasking.

II. Coiled Coils

Coiled coil forming peptides are peptide pairs that can associate with one another to form coiled coils. "Coiled coils" is a term of art referring to bundles of alpha-helices wound into superhelical structures. Leucine zipper forming peptides are one example of peptides associating to form coiled coils. The coiled coils formed in the present invention typically are formed from two coiled coil forming peptides. Coiled coils can form with alpha helices on the peptides in parallel or opposite orientations (examples of which are provided in FIGS. 1A and 1B). Coiled coils are further characterized by packing of amino acid side chains in the core of the bundle, called knobs-into-holes, in which a residue from one helix (knob) packs into a space surrounded by four side chains of the facing helix (hole). The residues engaged in knobs-into-holes interactions are usually hydrophobic, whereas the outer residues are hydrophilic, the sequence of coiled coils therefore shows a 'heptad' repeat in the chemical nature of side chains. Examples of consensus formulae for heptad repeats in coiled coils forming peptides are provided by WO2011034605.

$$(X1,X2,X3,X4,X5,X6,X7)n \qquad \text{Formula 1:}$$

X1 is a hydrophobic amino acid or asparagine
X2, X3 and X6 are any amino acid
X4 is a hydrophobic amino acid
X5 and X7 are each a charged amino acid residue $$(X1',X2',X3',X4',X5,X6,X7)n \qquad \text{Formula 2:}$$

X1' is a hydrophobic amino acid or asparagine
X2', X'3 and X'6 are each any amino acid residue
X4' is hydrophobic amino acid
X5' and X7' are each a charged amino acid residue
wherein n in formula 1 and 2 is greater or equal to 2; and
wherein each heptad repeat in the first coiled coil forming peptide comprises an X5 residue that is opposite in charge to the X'7 residue in the second coiled coil forming peptide and the first coiled coil forming peptide comprises an X7 residue that is opposite in charge to the X'5 residue in the second coiled coil forming peptide. Heptad repeats within a coiled coil forming peptide can be the same or different from each other while conforming to Formula 1 or 2.

Coiled-coils can be homodimeric or heterodimeric. Examples of pairs of coiled coil peptides are A2B1 GASTSVDELQAEVDQLQDENYALKTK-VAQLRKKVEKLSE, SEQ ID NO: 66 and GASTTVAQL-RERVKTLRAQNYELESEVQRLREQVAQLA, SEQ ID NO:67), CA2B1 EACGASTSVDELQAEVDQLQDE-NYALKTKVAQLRKKVEKLSE, SEQ ID NO: 68 and EACGASTTVAQLRERVKTLRAQNYELESEVQRL-REQVAQLA, SEQ ID NO:69), M11 LEIEAAFLEREN-TALETRVAELRQRVQRARNRVSQYRTRY, SEQ ID NO:26 and LEIRAAFLRQRNTALRTEVAELEQEVQR-LENEVSQYETRY, SEQ ID NO:21, CM11 EACGA-LEIEAAFLERENTALETRVAEL-RQRVQRARNRVSQYRTRY, SEQ ID NO: 39 and EACGALEIRAAFLRQRNTALRTEVAELEQEVQRLE-NEVSQYETRY, SEQ ID NO: 37, M15 LEIRAAFLRRRN-TALRTRVAELRQRVQRLRNIVSQYETRY, SEQ ID NO: 30 and LEIEAAFLEQENTALETEVAELEQEVQR-LENIVSQYETRY, SEQ ID NO: 28, CM15 EACGALEI-RAAFLRRRNTALRTRVAELRQRVQRLRNIVSQY-ETRY, SEQ ID NO: 43, and EACGALEIEAAFLEQENTALETEVAELEQEVQR-LENIVSQYETRY, SEQ ID NO: 41), Vel (Q)GASTSVDELQAEVDQLEDENYALKTK-VAQLRKKVEKL, SEQ ID NO: 35 and (Q)GASTTVAQLEEKVKTLRAENYELKSEVQRLE-EQVAQL, SEQ ID NO: 32, CVel EAC-GASTSVDELQAEVDQLEDENYALKTK-VAQLRKKVEKL, SEQ ID NO: 47 and EACGASTTVAQLEEKVKTLRAENYELKSEVQRLE-EQVAQL, SEQ ID NO: 45), Fos-Jun AGLTDTLQAETDQLEDKKSALQTE-IANLLKEKEKLEFILAAH, SEQ ID NO: 70 and AGRI-ARLEEKVKTLKAQNSELASTANML-REQVAQLKQKVMNY, SEQ ID NO: 71, CFos-Jun EACGAGLTDTLQAETDQLEDKKSALQTE-IANLLKEKEKLEFILAAH, SEQ ID NO: 72 and EACGAGRIARLEEKVKTLKAQNSELASTANML-REQVAQLKQKVMNY, SEQ ID NO:73, A4B4 GKI-AALKQKIAALKYKNAALKKKIAALKQ, SEQ ID NO: 74 and GEIAALEQEIAALEKENAALEWEIAALEQ, SEQ ID NO:75, and CA4B4 EACGAGKIAALKQKIAALKYK-NAALKKKIAALKQ, SEQ ID NO:76 and EACGAGE-IAALEQEIAALEKENAALEWEIAALEQ, SEQ ID NO:77.

Figure 1A:
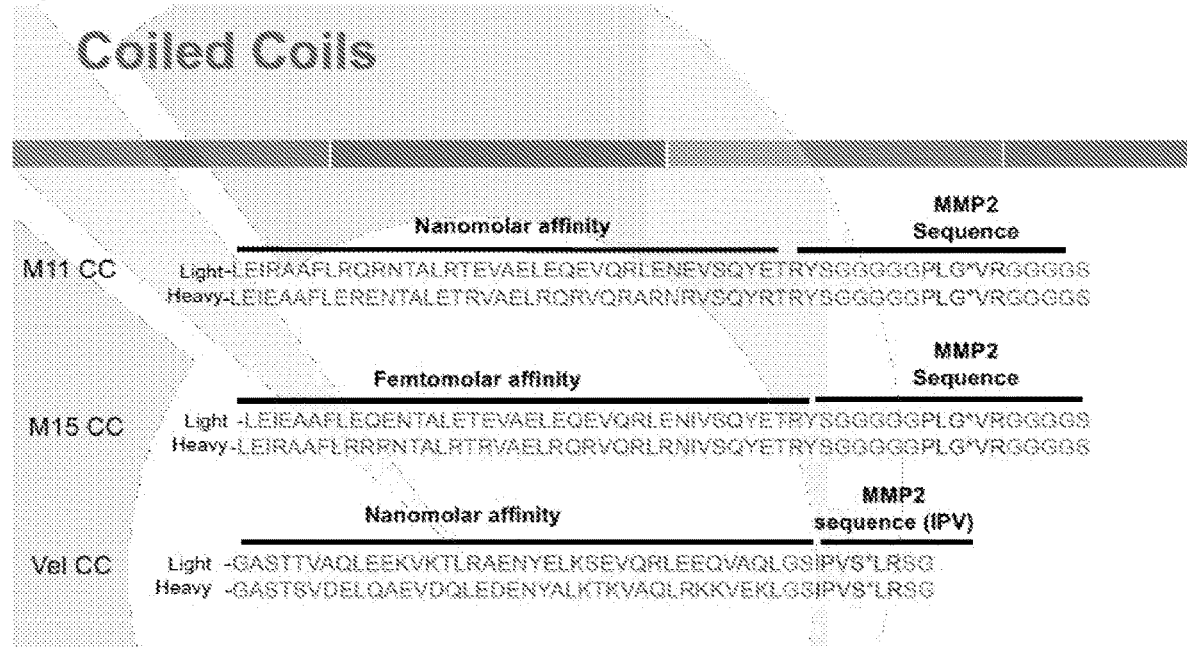
Figure 4:
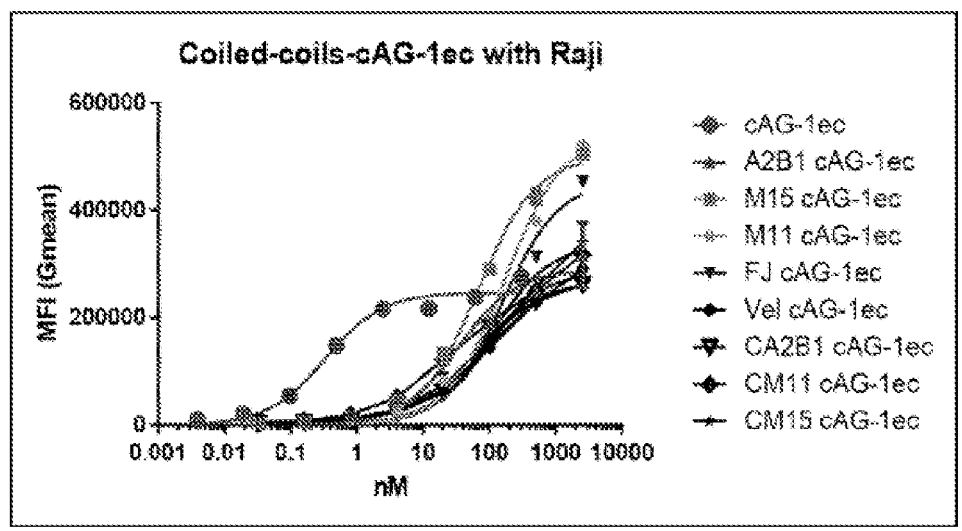
FIG. 4 shows masked anti-antigen 1 antibodies binding to antigen 1-positive cells using FACs-based saturation binding assays.

Some examples of pairs of coiled-coil forming peptides are also shown in Table 1 and in FIGS. 1A and 1B. Hyphens within the sequences shown in FIGS. 1A and 1B delineate different segments of the sequences. From left to right, the sequences are coiled coil peptide, artificial linker, protease cleavage site within artificial linker and remainder of artificial linker. The peptide sequences can be used as is, or their components can be used in other combinations. For example, the Vel coiled coil forming peptide can be used with other linker sequences. Sequences shown for light chains can also be used with heavy chains and vice versa.

A preferred combination is a peptide comprising or consisting of amino acids of SEQ ID NO: 44 ((CVelCC in FIG. 1B) to provide a linker including a protease cleavage site and a coiled-coil forming peptide linked to the light chain and a peptide of sequence SEQ ID NO: 46 (CVel CC FIG. 1B): to provide a linker including a protease cleavage site and the coiled-coil forming peptide linked to the heavy chain, or vice versa. Peptides consisting of comprising these sequences can be linked to any of the antibodies disclosed herein.

Another preferred combination is a peptide comprising or consisting of amino acids of SEQ ID NO: 31 ((VelCC) or SEQ ID NO:65 (without the N-terminal Q) to provide a linker including a protease cleavage site and a coiled-coil forming peptide linked to the light chain and a peptide of sequence SEQ ID NO: 34 (Vel CC) or SEQ ID NO:64 (without the N-terminal Q) to provide a linker including a protease cleavage site and the coiled-coil forming peptide linked to the heavy chain, or vice versa. Peptides consisting of comprising these sequences can be linked to any of the antibodies disclosed herein.

TABLE 1

| Coiled-coils forming peptides | |
|---|---|
| Coil Name | Paper |
| Fos/Jun | Pluckthun et.al., Immunotechnology 1997, 3, 83-105 |
| A3B3 | Thomas et.al., J. Am. Chem. Soc. 2013, 135, 5161-516 |
| A4B4 | Thomas et.al., J. Am. Chem. Soc. 2013, 135, 5161-516 |
| IAAL3 | Litowski et. al., J. Biol. Chem. 2002, 277, 37272-37279 |
| CVel | Arndt et.al., Structure 2002 10, 1235-1248; Schmidt, *Engineering antibodies for improved targeting of solid tumors*, Thesis, 2010 |
| antipO | McClain et.al., J. Am. Chem. Soc. 2001, 123, 3151-3152 |
| dHLX | Pluckthun et.al., Immunotechnology 1997, 3, 83-105 |
| Vel | Arndt et.al., Structure 2002 10, 1235-1248 |
| A2B1 | Arndt et.al., Structure 2002 10, 1235-1248 |
| M15 | Moll et.al., Protein Science 2001, 10, 649-655 |
| M11 | Moll et.al., Protein Science 2001, 10, 649-655 |

Variants of these peptides having at least 80%, 90% or 95% identity thereto and still capable of forming a coiled-coil can also be used. Any substitutions are preferably conservative substitutions. Preferably a repeating heptad patterns is retained whereby a coiled coil forming peptide can be subdivided into contiguous heptad segments conforming to a formula categorizing amino acids occupying positions in the formula by amino acid type, such as that shown above. Preferably there are no more than 1 or 2 substitutions per heptad of amino acids, and any such substitutions are conservative.

In any coiled coil peptide sequence in which the N-terminal residue is Q, the Q is optional. In any coiled coil peptide sequence in which the N-terminal residue is other than Q, a Q can be added forming the N-terminal residue. Presence of Q as the N-terminal residue can facilitate signal sequence processing.

III. Linkers and Cleavage Sites

The linkers can be any segments of amino acids conventionally used as linker for joining peptide domains. Suitable linkers can vary in length, such as from 1-20, 2-15, 3-12, 4-10, 5, 6, 7, 8, 9 or 10. Some such linkers include a segment of polyglycine. Some such linkers include one or more serine residues, often at positions flanking the glycine residues. Other linkers include one or more alanine residues. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Some exemplary linkers are in the form S(G)nS, wherein n is from 5-20. Other exemplary linkers are (G)n, glycine-serine polymers (including, for example, (GS)n, (GSGGS)n [(GSGGS) is SEQ ID NO: 49) and (GGGS)n, [(GGGS) is SEQ ID NO: 50) where n is an integer of at least one), glycine-alanine polymers, alanine-serine polymers, and other flexible linkers known in the art. Some examples of linkers are Ser-(Gly) 10-Ser (SEQ ID NO: 51), Gly-Gly-Ala-Ala (SEQ ID NO: 52), Gly-Gly-Gly-Gly-Ser (SEQ ID NO: 24), Leu-Ala-Ala-Ala-Ala (SEQ ID NO: 53), Gly-Gly-Ser-Gly (SEQ ID NO: 54), Gly-Gly-Ser-Gly-Gly (SEQ ID NO: 55), Gly-Ser-Gly-Ser-Gly (SEQ ID NO: 56), Gly-Ser-Gly-Gly-Gly (SEQ ID NO: 57), Gly-Gly-Gly-Ser-Gly (SEQ ID NO: 58), Gly-Ser-Ser-Ser-Gly (SEQ ID NO: 59), and the like.

The protease site is preferably recognized and cleaved by a protease expressed extracellularly so it contacts a masked antibody, releasing the masked antibody and allowing it to contact its target, such as a receptor extracellular domain or soluble ligand. Several matrix metalloproteinase sites (MMP1-28) are suitable. MMPs play a role in tissue remodeling and are implicated in neoplastic processes such as morphogenesis, angiogenesis and metastasis. Some exemplary protease sites are PLG-XXX (SEQ ID NO: 60), a well-known endogenous sequence for MMPs, PLG-VR (SEQ ID NO: 23) (WO2014193973), IPVSLR (SEQ ID NO: 33) (Turk et al., Nat. Biotechnol., 2001, 19, 661-667), LSGRSDNH (SEQ ID NO: 61) (Cytomyx), GPLGVR (SEQ ID NO: 62) (Chang et al., Clin. Cancer Res. 2012 Jan. 1; 18(1):238-47). VPMS-MRGG (MMP1, SEQ ID NO: 78), RPFS-MIMG (MMP3, SEQ ID NO:79), IPES-LRAG (MMP14, SEQ ID NO: 80), -VPLS*LTMG (SEQ ID NO: 81) (Turk et al., Nat. Biotechnol., 2001, 19, 661-667). Other exemplary protease sites are PLGLAG (SEQ ID NO: 82), LALGPG (SEQ ID NO: 83), and YGRAA (SEQ ID NO: 84), Additional examples are provided in earlier work, such as US2013/0309230, WO2009/025846, WO2010/081173, WO2014/107599, WO2015/048329, US20160160263, and Ratnikov et al., Proc. Natl. Acad. Sci. USA, 111: E4148-E4155 (2014).

Some examples of coiled coil forming peptides attached to linkers including protease sites are shown in FIGS. 1A and 1B. The components of such peptides are separated by hyphens (i.e., coiled coil forming peptide-left hand part of linker-protease site-right hand part of linker.

IV. Antibodies and Linkage of Antibodies to Coiled Coils

Coiled coils forming peptides are linked to the N-termini of antibody variable regions via a linker including a protease site. A typical antibody includes a heavy and light chain variable region, in which case a coiled-coil forming peptide is linked to the N-termini of each. A bivalent antibody has two binding sites, which may or may not be the same. In a normal monospecific antibody, the binding sites are the same and the antibody has two identical light and heavy chain pairs. In this case, each heavy chain is linked to the same coiled-coil forming peptide and each light chain to the same coiled-coil forming peptide (which may or may not be the same as the peptide linked to the heavy chain).

In a bispecific antibody, the binding sites are different and formed from two different heavy and light chain pairs. The binding sites can have specificity for different targets or different epitopes on the same target. If the binding sites have specificity for different targets, the targets can be on the same cell (e.g., two different surface antigens on a cancer cell) or two different cells (e.g., one surface antigen on a cancer cell and one on an immune cell such as a T-cell). For example, one binding site of a bispecific antibody can be directed against CD3 or 4-1BB.

In a bispecific antibody, the heavy and light chain variable region of one binding site can be respectively linked to coiled-coil forming peptides. The heavy and light chain variable regions of the other binding site may or may not be also linked to coiled coil peptides. If the heavy light pairs of both binding sites are both linked to coiled coil peptides, then typically both heavy chain variable regions are linked to the same type of coiled-coil forming peptide as are both light chain variable regions. Masking of both binding sites can be useful, for example, if both binding sites have specificity for surface antigens on the same tumor. Masking of one but not both binding sites can be useful for example, when one binding site is specific for a tumor surface antigen and the other has specificity for a surface antigen on an immune cell. Either the binding site with specificity for the tumor surface antigen or for the immune cell antigen can be masked. Some bispecific antibodies with specificities to both a tumor surface antigen and an immune cell have masking of both sites.

As noted, a coiled coil forming peptide is linked to an antibody variable region via a linker including a protease site. Typically the same linker with the same protease cleavage site is used for linking each heavy or light chain variable region of an antibody to a coiled-coil peptide. The protease cleavage site should be one amenable to cleavage by a protease present extracellularly in the intended target tissue or pathology, such as a cancer, such that cleavage of the linker releases the antibody from the coiled-coil masking its activity allowing the antibody to bind to its intended target, such as a cell-surface antigen or soluble ligand.

As well as the variable regions, a masked antibody typically includes all or part of a constant region, which can include any or all of a light chain constant region, CH1, hinge, CH2 and CH3 regions. As with other antibodies one or more C-terminal residues can be proteolytically processed or derivatized.

Coiled coils can be formed from the same peptide forming a homodimer or two different peptides forming a heterodimer. For formation of a homodimer, light and heavy antibody chains are linked to the same coiled coil forming peptide. For formation of a heterodimer, light and heavy antibody chains are linked to different coiled coils peptides. For some pairs of coiled coil forming peptides, it is preferred that one of the pair be linked to the heavy chain and the other to the light chain of an antibody although the reverse orientation is also possible.

Each antibody chain can be linked to a single coiled coil forming peptide or multiple such peptides in tandem (e.g., two, three, four or five copies of a peptide). If the latter, the peptides in tandem linkage are usually the same. Also if tandem linkage is employed, light and heavy chains are usually linked to the same number of peptides.

Linkage of antibody chains to coiled coil forming peptides can reduce the binding affinity of an antibody by, for example, at least 10, 50, 100, 200, 500, 1000, 1500, 2000, 4000, 5000 or 10,000-fold relative to the same antibody without such linkage or after cleavage of such linkage. In some such antibodies, binding affinity is reduced 50-10,000, 50-5000, 50-4000, 50-1000, 100-10,000, 100-5000, 100-4000, 200-10,000, 200-5000, 50-1500, 100-1500, 200-1500, 200-1000, 500-1500, 50-1000, 100-1000, 200-1000, 500-

1000, 50-500, 100-500 fold. Effector functions of the antibody, such as ADCC, phagocytosis, and CDC or cytotoxicity as a result of linkage to a drug in an antibody drug conjugate can be reduced by the same factors or ranges. On proteolytic cleavage unmasking an antibody, the restored antibody can have an affinity or effector function that is within a factor of 5, 2, 1.5 or preferably unchanged within experimental error compared with an otherwise identical control antibody, which has never been masked.

V. Antibody Drug Conjugates

As well as linkage to naked antibodies, coiled-coil forming peptides can be linked to antibodies conjugated to cytotoxic or cytostatic moieties as antibody drug conjugates (ADCs). In comparison with naked antibodies, ADCs provide additional mechanisms, particularly delivery of a toxic moiety coupled to the antibody to the interior of a cell, thereby killing the cell or otherwise inhibiting its proliferation. Currently two ADCs are marketed: brentuximab vedotin (anti-CD30 trade name: ADCETRIS®, marketed by Seattle Genetics and Millennium/Takeda) and trastuzumab emtansine (anti-HER2, trade name: Kadcyla®, marketed by Genentech and Roche). Many other ADCs are at various stages of development.

Techniques for conjugating drugs to antibodies are well-known (see, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Dekker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g. WO 89/12624).

Drugs are usually conjugated either via amino groups on lysine side chains or free sulfydryl groups on cysteine side chains. The cysteine residues can be naturally present in an antibody (e.g., interchain disulfides) or introduced by mutagenesis. Cysteine contains a free sulfhydryl group, which is more nucleophilic than amines and is generally the most reactive functional group in a protein. Sulfhydryls, unlike most amines, are generally reactive at neutral pH, and therefore can be coupled to other molecules selectively in the presence of amines. This selectivity makes the sulfhydryl group the linker of choice for coupling antibodies. The mean number of molecules drug per molecule antibody is often 1, 2, 3, 4, 5, 6, 7, or 8, e.g., from 2-8 or 3-8.

The drug can be conjugated in a manner that reduces its activity unless it is cleaved off the antibody (e.g., by hydrolysis, by antibody degradation or by a cleaving agent). Such a drug is attached to the antibody with a cleavable linker that is sensitive to cleavage in the intracellular environment of a target cell but is not substantially sensitive to the extracellular environment, such that the conjugate is cleaved from the antibody when it is internalized by the target cell (e.g., in the endosomal or, for example by virtue of pH sensitivity or protease sensitivity, in the lysosomal environment or in the caveolear environment).

Typically the ADC comprises a linker region between the drug and the antibody. The linker may be cleavable under intracellular conditions, such that cleavage of the linker releases the drug from the antibody in the intracellular environment (e.g., within a lysosome or endosome or caveolea). The linker can be, e.g., a peptidyl linker cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, *Pharm. Therapeutics* 83:67-123). Most typical are peptidyl linkers that are cleavable by enzymes that are present in target cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly (SEQ ID NO: 63) peptide). Other such linkers are described, e.g., in U.S. Pat. No. 6,214,345. An exemplary peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular protease release of the drug is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. One example of such a hydrolyzable linker is a thioether linker (such as, e.g., a thioether attached to the drug via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935).

The linker can also be a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

The linker also can be a non-cleavable linker, such as a maleimido-alkylene- or maleimide-aryl linker that is directly attached to the drug (e.g., a drug). An active drug-linker is released by degradation of the antibody.

The linker is one that that comprises a functional group that is reactive to a group present on the antibody. For example, the linker can be linked to the antibody via a disulfide bond between a sulfur atom of the linker and a sulfur atom of the antibody. As another example, the linker can form a bond with a sulfur atom of the antibody via a maleimide group of the Stretcher Unit. The sulfur atom can be from a cysteine residue of an interchain disulfide or from a cysteine residue introduced into the antibody.

Useful classes of cytotoxic agents to conjugate to antibodies include, for example, antitubulin agents, DNA minor groove binding agents, DNA replication inhibitors, chemotherapy sensitizers, a pyrrolobenzodiazepine dimer or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin E, AFP, MMAF, MMAE), DNA minor groove binders (e.g., enediynes and lexitropsins), duocarmycins, taxanes (e.g., paclitaxel and docetaxel), vinca alkaloids, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of various auristatins are described in, for example, US 2005-0238649 and U52006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin). Another class of minor groove binding agents are pyrrolobenzodiazepine (PBD) dimers. PBDs exert their biological activity through covalent binding via their N10-C11 imine/carbinolamine moieties to the C2-amino position of a guanine residue within the minor groove of DNA.

PBDs are of the general structure:

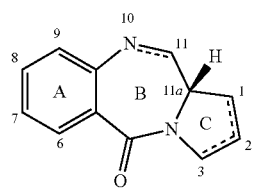

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position, which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumor agents.

The biological activity of these molecules can be potentiated by joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand cross-link, which is thought to be mainly responsible for their biological activity.

In some embodiments, PBD based antibody-drug conjugates comprise a PBD dimer linked to an antibody. The monomers that form the PBD dimer can be the same or different, i.e., symmetrical or unsymmetrical. The PBD dimer can be linked to the antibody at any position suitable for conjugation to a linker. For example, in some embodiments, the PBD dimer will have a substituent at the C2 position that provides an anchor for linking the compound to the antibody. In alternative embodiments, the N10 position of the PBD dimer will provide the anchor for linking the compound to the antibody.

Typically the PBD based antibody-drug conjugate comprises a linker between the PBD drug and the antibody binding to the antigen of the primary cancer. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in WO 2011/130613 and is as follows wherein the wavy line indicates the site of attachment to a linker:

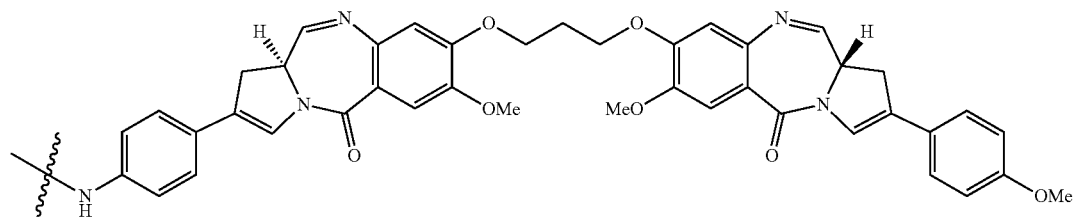 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

or a pharmaceutically acceptable salt thereof. An exemplary linker is as follows wherein the wavy line indicates the site of attachment to the drug and the antibody is linked via the maleimide group.

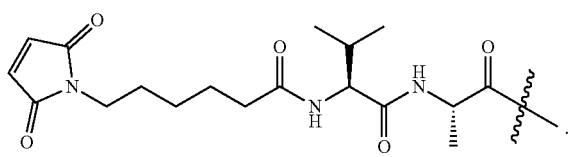 [SMILES: *C(=O)[C@H](C)NC(=O)[C@@H](NC(=O)CCCCCN1C(=O)C=CC1=O)C(C)C]

Exemplary PBDs based antibody-drug conjugates include antibody-drug conjugates as shown below wherein Ab is an antibody as described herein:

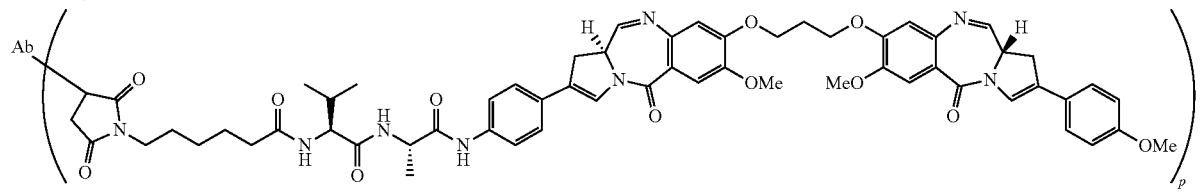

or a pharmaceutically acceptable salt thereof. The drug loading is represented by p, the number of drug-linker molecules per antibody.

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Exemplary auristatins are shown below in formulae III-XIII Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

The cytotoxic agent can be a maytansinoid, another group of anti-tubulin agents. For example, the maytansinoid can be maytansine or a maytansine containing drug linker such as DM-1 or DM-4 (ImmunoGen, Inc.; see also Chari et al., 1992, *Cancer Res.* 52:127-131).

Exemplary antibody drug conjugates include vcMMAE and mcMMAF antibody drug conjugates as follows, or pharmaceutically acceptable salts thereof, wherein p represents the drug loading and ranges from 1 to 20 and Ab is an antibody:

VI. Targets

Antibodies include non-human, humanized, human, chimeric, and veneered antibodies, nanobodies, dAbs, scFV's, Fabs, and the like. Some such antibodies are immuno specific for a cancer cell antigen, preferably one on the cell surface internalizable within a cell on antibody binding. Targets to which antibodies can be directed include receptors on cancer cells and their ligands or counter-receptors (e.g., CD3, CD19, CD20, CD22, CD30, CD33, CD34, CD40, CD44, CD52, CD70, CD79a, CD123, Her-2, EphA2, lymphocyte associated antigen 1, VEGF or VEGFR, CTLA-4, LIV-1, nectin-4, CD74, and SLTRK-6).

Some examples of commercial antibodies and their targets suitable for application of the present methods include brentuximab or brentuximab vedotin, CD30, alemtuzumab, CD52, rituximab, CD20, trastuzumab Her/neu, nimotuzumab, cetuximab, EGFR, bevacizumab, VEGF, palivizumab, RSV, abciximab, GpIIb/IIIa, infliximab, adalimumab, certolizumab, golimumab TNF-alpha, basiliximab, daclizumab, IL-2, omalizumab, IgE, gemtuzumab or vadastuximab, CD33, natalizumab, VLA-4, vedolizumab alpha4beta7, belimumab, BAFF, otelixizumab, teplizumab CD3, ofatumumab, ocrelizumab CD20, epratuzumab CD22, alemtuzumumab CD52, eculizumab C5, canakimumab IL-1beta, mepolizumab IL-5, reslizumab, tocilizumab IL-6R, ustekinumab, briakinumab IL-12, 23, hBU12 (CD19) (US20120294853), humanized 1F6 or 2F12 (CD70) (US20120294863), BR2-14a and BR2-22a (LIV-1) (WO2012078688). Some sequences of exemplary antibodies are provided in the sequence listing.

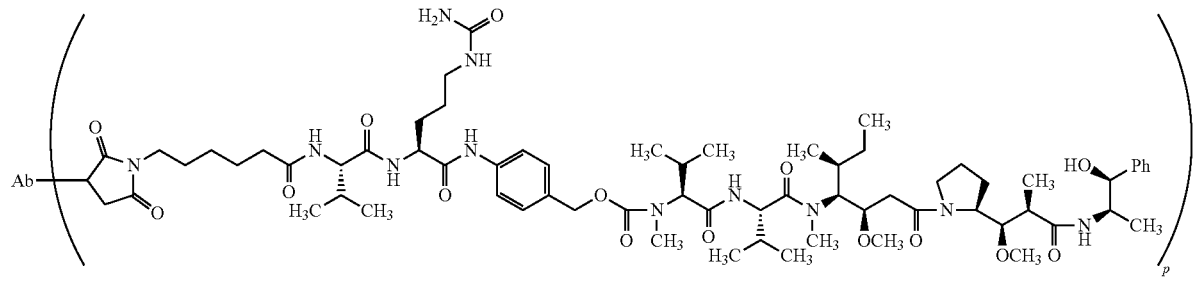

vcMMAE

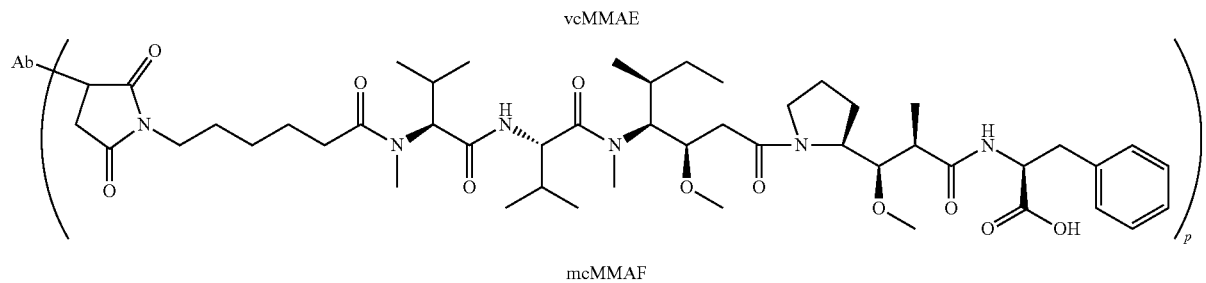

mcMMAF

VII. Pharmaceutical Compositions and Methods of Treatment

Masked antibodies (including masked naked antibodies and ADC's) produced in accordance with the methods described above are administered in an effective regime meaning a dosage, route of administration and frequency of administration that delays the onset, reduces the severity, inhibits further deterioration, and/or ameliorates at least one sign or symptom of the disease it is intended to treat, such as cancer, autoimmune disease or infection including any of the indications discussed above. If a patient is already suffering from the disease, the regime can be referred to as a therapeutically effective regime. If the patient is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a pre-clinical or clinical trial in a population of treated patients relative to a control population of untreated patients.

Exemplary dosages for a masked antibody are 1 mg/kg to 100 mg/kg, 5 mg-50 mg/kg, 10 mg-25 mg/kg, 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-15000, 200-15000 or 500-10,000 mg as a fixed dosage. In some methods, the patient is administered a dose of at least 1.5 mg/kg, at least 2 mg/kg or at least any of 3 mg/kg, 4 mg/kg, 5 mg/kg, 6 mg/kg, 7 mg/kg, 8 mg/kg, or 9 mg/kg or 10 mg/kg administered once every three weeks or greater. Exemplary dosages for masked active monoclonal antibody drug conjugates thereof, e.g., auristatins, are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. Exemplary dosages for highly active masked monoclonal antibody drug conjugates thereof, e.g., PBDs, are 1.0 µg/kg to 1.0 mg/kg, or 1.0 µg/kg to 500.0 µg/kg of the subject's body weight. In some methods, the patient is administered the masked ADC every two, three or four weeks. The dosage depends on the frequency of administration, condition of the patient and response to prior treatment, if any, whether the treatment is prophylactic or therapeutic and whether the disorder is acute or chronic, among other factors. The dose also depends on the decrease in binding, effector function or cytotoxicity. In general, larger dosages of masked antibodies can be administered than the same antibodies without the masking.

Administration can be parenteral, intravenous, oral, subcutaneous, intra-arterial, intracranial, intrathecal, intraperitoneal, topical, intranasal or intramuscular. Administration can also be localized directly, such as into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the masked antibody in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the disease (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic (240-360 mOsm/kg) and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, masked antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with masked antibodies of the invention can be combined with chemotherapy, radiation, stem cell treatment, surgery, anti-virals, antibiotics, immune suppressants or stimulants, or other treatments effective against the disorder being treated. Useful classes of other agents that can be administered with ADC's for treatment of cancers or auto-immune disease include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the masked antibodies can increase the median progression-free survival or overall survival time of patients with tumors, especially when relapsed or refractory, by at least 30% or 40% but preferably 50%, 60% to 70% or even 100% or longer, compared to the same treatment (e.g., chemotherapy) but without a masked antibody. In addition or alternatively, treatment (e.g., standard chemotherapy) including the masked antibody can increase the complete response rate, partial response rate, or objective response rate (complete+partial) of patients with tumors by at least 30% or 40% but preferably 50%, 60% to 70% or even 100% compared to the same treatment (e.g., chemotherapy) but without the masked antibody.

Typically, in a clinical trial (e.g., a phase II, phase II/III or phase III trial), the aforementioned increases in median progression-free survival and/or response rate of the patients treated with standard therapy plus the masked antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

Although the invention has been described in detail for purposes of clarity of understanding, it will be obvious that certain modifications may be practiced within the scope of the appended claims. All publications, accession numbers, web sites, patent documents and the like cited in this application are hereby incorporated by reference in their entirety for all purposes to the same extent as if each were so individually denoted. To the extent different information is associated with a citation at different times, the information present as of the effective filing date of this application is meant. The effective filing date is the date of the earliest priority application disclosing the accession number in question. Unless otherwise apparent from the context any element, embodiment, step, feature or aspect of the invention can be performed in combination with any other.

EXAMPLES

Example 1: Preparation and Characterization of Masked Antibodies

All chemicals were purchased from Sigma Aldrich unless otherwise noted. All proteases were purchased from R&D Systems with the exception of human MMP2 (Sino Biological). Protease inhibitors were purchased from EMD Millipore unless otherwise stated. Pyrrolobenzodiazepine (PBD)-linker containing a maleimide was prepared as previously reported. (Jeffrey et. al., *Bioconjugate Chemistry*, 2013, 24, 1256-1263.) Mc-MMAF-linker was prepared as reported in CD19 studies (e.g., US20120294853).

Antibody Production

Antibodies were expressed via transient transfection or stable transfection of Expi HEK cells, Expi-CHO, or CHO-DG44 cells and purified using MABSELECT™ SURE™ columns (GE Healthcare), size-exclusion chromatography, and a post-Protein A method. Each antibody produced contained an engineered cysteine (S239C) in the heavy chain constant region. The names of S239C constant region mutants include the designation ec. Sequences of antibodies are provided in the sequence listing.

Antibodies were fluorescently labeled using ALEXA FLUOR® 488 or 647 NHS Ester (Life Technologies, A20000, A20006) following vendor protocol. Briefly, antibody (1eq) was incubated with fluorophore (4 eq) at pH 8 for 1 hour at room temperature (RT). Fluorescent antibody was purified using a NAP™ 5 column (GE Healthcare Life Sciences, 17-0853-02) and fluorophore loading was measured using UV-Vis (Agilent). Typical fluorophore loadings were 3-5 fluorophores per antibody.

Competition Binding Experiments

To evaluate cell binding of masked antibodies, $2 \times 10^5$ of indicated cells (Raji, Ramos, PC3, Daudi) were combined with fluorescently labeled parent antibody mixed with serial dilutions of competitor (masked antibody) in staining buffer (PBS, 2% FBS, 0.2% NaN3). Samples were incubated for 1 hour on ice and washed twice with ice-cold staining buffer. Labeled cells were examined by flow cytometry on a BD LSRII gated to exclude nonviable cells and analyzed using Flowing Software (Turku Centre for Biotechnology). The $IC_{50}$ was calculated using GraphPad Prism 6.

Four antibodies (hBU12 against CD19, anti-Antigen 1 antibody against Antigen 1 (cAg-1), 1C1 against EphA2 and HuMab CD74-011 against CD74) were tested using the coiled coil blocking domains. The antibody CD74 comprises a light chain (SEQ ID NO: 1) and a heavy chain (SEQ ID NO: 2). Sequences for A3B3, A4B4, CVel, antipO, and dHLX were N-terminally fused to the light and heavy chains of the antibodies. To test for binding, FACs-based competition assays were utilized to account for high concentrations of competitor necessary to displace the parent antibody and the results are listed in Tables 2-5. Other antibodies that can be conjugated to a coiled-coil peptide are SEQ ID NOs: 3-19. SEQ ID NO: 3 is the amino acid sequence of hBU12 heavy chain variable region, and SEQ ID NO: 4 is the amino acid sequence of hBU12 light chain variable region. SEQ ID NO: 5 is the amino acid sequence of 2H12 LG light chain variable region, and SEQ ID NO: 6 is the amino acid sequence of 2H12 HI heavy chain variable region. SEQ ID NO: 7 is the amino acid sequence of light chain constant region; PRT/1; *Homo sapiens*. SEQ ID NO: 8 is the amino acid sequence of CH1-CH3; PRT/1; *Homo sapiens*. SEQ ID NO: 9 is the amino acid sequence of heavy chain CH1-CH3 (no c-term K); PRT/1; *Homo sapiens*. SEQ ID NO: 10 is the amino acid sequence of S239C heavy chain CH1-CH3; PRT/1; *Homo sapiens*. SEQ ID NO: 11 is the amino acid sequence of S239C heavy chain CH1-CH3 (no c-term K); PRT/1; *Homo sapiens*. SEQ ID NO: 12 is the amino acid sequence of heavy chain variable region for h7G3, CD123 Ab, and SEQ ID NO: 13 is the amino acid sequence of light chain variable region for h7G3, CD123 Ab. SEQ ID NO: 14 is the amino acid sequence of H1F6 light chain variable region, CD70 Ab, and SEQ ID NO: 15 is H1F6 heavy chain variable region, CD70 Ab. SEQ ID NO: 16 is the amino acid sequence of mature light chain variable region of humanized 20F3 LD, CD352 Ab, and SEQ ID NO17 is the amino acid sequence of the mature heavy chain variable region of humanized 20F3 HD, CD352 Ab. SEQ ID NO: 18 is the amino acid sequence of hLiv1 mAb2 HG; PRT/1; artificial, and SEQ ID NO: 19 is the amino acid sequence of hLiv1 mAb2 LG; PRT/1; artificial.

TABLE 2

| $IC_{50}$ values of various masked antibodies binding to Raji cells ||| 
|---|---|---|
| MAb | $IC_{50}$ (nM) | Fold Change |
| hBU12ec | 3.6 | — |
| A3B3 hBU12ec | 298 | 83 |
| A4B4 hBU12ec | >1000 | >300 |
| Cvel hBU12ec | >1000 | >300 |
| AntipO hBU12ec | 138 | 38 |
| dHLX hBU12ec | >1000 | >300 |
| Hinge hBU12ec | 971 | 269 |
| Hinge noncleavable hBU12ec | 602 | 167 |

TABLE 3

IC$_{50}$ values of various masked antibodies binding to Ramos cells (antigen-1 mAbs)

| mAb | IC$_{50}$ (nM) | Fold Change |
|---|---|---|
| cAg-1ec | 1.3 | — |
| Hinge cAg-1ec | 60 | 46 |
| A3B3 cAg-1ec | 45 | 34 |
| A4B4 cAg-1ec | 1205 | 927 |
| Cvel cAg-1ec | 1389 | 1068 |
| antipO cAg-1ec | 34 | 26 |
| dHLX cAg-1ec | 302 | 233 |

Binding of masked hBU12 antibodies was assessed on CD19-positive Raji cells. A variety of coiled-coils were tested, e.g., A3B3, A4B4, antipO, and dHLX, as was a hinge blocker. See, e.g., Table 1 and WO2014/193973. There is an apparent distinction between coiled-coil affinity and blocking ability for the parallel homodimeric blocking domains. A3B3 (micromolar affinity coil) decreased the binding of the antibody by 83 fold whereas the higher affinity femtomolar and covalent coils (A4B4 and CVel) decreased binding by over 300 fold. The antiparallel coil (antipO) did not block with a 38-fold decrease in binding. The helix-turn-helix blocking domain (dHLX) displayed over 300 fold decrease in binding and the hinge-blocker had a 269-fold decrease. In the hBu12 example, the A3B3 and antipO coils blocked less as compared to the other coils and hinge, but it was difficult to parse out the blocking ability of the remaining domains.

The masked-cAg-1 antibodies provided a more discerning look into the blocking ability of the coiled coils. The hinge, A3B3, and antipO-blocked cAg-1 antibodies blocked binding by 20 to 50-fold. The dHLX-blocked cAg-1 was capable of decreasing binding by 233-fold. A4B4 and CVel, the two highest affinity coiled coils displayed the highest fold change of approximately 1000-fold decrease in binding. From this data, the parallel coils with high-affinity displayed the best blocking ability and had been moved forward for further testing of other antibodies.

In the experiments testing 1C1 against EphA2 and HuMab-CD74-011 against CD74, the antibodies were shown to be difficult to block. The CVel masking domain decreased binding by 43-fold for 1C1 and 26-fold for HuMab-CD774-01. The dHLX masking domain decreased binding of 1C1 to EphA2 by 16-fold and the hinge blocker decreased binding of HuMab-CD74-011 to CD74 by 14-fold. The remaining masking domains tested were unable to change the binding of the antibody (0.6 to 6-fold change). To improve on the blocking panel, a second generation of coiled-coils masking domains were designed.

The second generation of blocking domains were all parallel coiled coils with nanomolar affinity or higher between the two peptides. Additionally, to test the contribution of the N-terminal disulfide on blocking ability, each coiled coil was designed with an N-terminal cysteine. Four new coiled-coil pairs (with and without N-terminal cysteine) and Vel (the cysteine-less version of CVel) were appended to an antibody directed against antigen 1 and tested for blocking. All five coiled-coil pairs (with and without N-terminal cysteine) were capable of decreasing binding of the antibody by >200-fold. These binding experiments indicated that coiled-coil-based masking domains are generally successful given the coils are parallel with nanomolar affinity or higher.

Saturation Binding Experiments

2×10$^5$ of indicated cells (Raji, SW780, HT1080) were combined with a serial dilution of indicated antibody in staining buffer (PBS, 5% FBS, 0.2% NaN3). Samples were incubated for 1 hour on ice and washed twice with ice-cold staining buffer. Cells were resuspended with anti-human IgG-AF647 (Jacksonimmuno, 1:200 dilution in staining buffer) for 1 hour on ice. Cells were washed twice with ice cold staining buffer and resuspended in staining buffer. Labeled cells were examined by flow cytometry on a BD LSRII gated to exclude nonviable cells and analyzed using Flowing Software (Turku Centre for Biotechnology). The Kd was calculated using GraphPad Prism 6.

The second generation of masked cAg-1 antibodies was also tested for binding using FACs-based saturation binding assays to antigen 1-positive Raji cells. As shown in Table 4 and FIG. 4, the blocking of cAg-1 was variable depending on the coiled coil pair used. A2B1 cAg-1 decreased binding by 101-fold, M15 by 201-fold, and Vel by 279-fold. M11 and Fos/Jun decreased binding 520-fold and 472-fold respectively. There was no distinct advantage toward adding the N-terminal disulfide for M11 and M15, which resulted in a lower fold difference in binding. For A2B1, addition of the N-terminal linkage doubled the decrease in binding.

Similar studies were also conducted in HT1080 cells and SW780 cells. The Kd values are summarized in Tables 6 and 7. In some cases, non-specific binding was observed, presumably due to the coiled-coil domain interacting with the cell surface. As such, no Kd could be accurately determined, and these instances are denoted by *N/A. As shown in Table 5 in HT1080 cells, A2B1 cAg-1 decreased binding by 514-fold, M15 cAg-1 by 549-fold, and M11 cAg-1 by 1336-fold. There was no distinct advantage toward adding the N-terminal disulfide for A2B1 and M15. As shown in Table 6 in SW780 cells, A2B1 cAg-1 decreased binding by 101-fold, M15 cAg-1 by 153-fold, M11 cAg-1 by 216-fold, and Vel by 252-fold.

The binding of unmasked and coiled-coil masked anti-human Ag2 antibodies were also evaluated on HT1080, HCT116, and SW780 cell lines by flow cytometry. An increasing concentration of each masked antibody was added to antigen positive cells and incubated for 30 min on ice. Bound antibodies were detected using a fluorophore-labeled anti-human Fc antibody and the data was plotted using GraphPad Prism. The Kd values are summarized in Tables 8-10. As shown in Table 7 in HT1080 cells, A2B1 cAg-2, M15 cAg-2, M11 cAg-2, and Vel cAg-2 decreased the binding at least by 95-fold. By comparing the effects of masking of anti-Ag2 using either CVel or Vel coiled coil in three different cell lines, the data showed that the Vel coiled-coil inhibited binding to a greater extent than CVel (FIGS. 7A-C).

TABLE 4

| Kd values of masked antibodies binding to Raji cells | | |
|---|---|---|
| Antibody | Kd (nM) | Fold Change |
| cAg-1ec | 0.3 | 1 |
| A2B1 cAg-1ec | 33.0 | 101 |
| M15 cAg-1ec | 65.5 | 201 |
| M11 cAg-1ec | 169.5 | 520 |
| Fos/Jun cAg-1ec | 153.9 | 472 |
| Vel cAg-1ec | 90.9 | 279 |
| CA2B1 cAg-1ec | 73.2 | 224 |
| CM11 cAg-1ec | 33.0 | 101 |
| CM15 cAg-1ec | 104.1 | 319 |

TABLE 5

Kd values of masked antibodies binding to HT1080 cells

| Antibody | Kd (nM) | Fold change |
|---|---|---|
| Anti-Ag1 | 1.1 | — |
| A2B1-Anti-Ag1 | 531 | 483 |
| CA2B1-Anti-Ag1 | 566 | 514 |
| M15-Anti-Ag1 | 469 | 426 |
| CM15-Anti-Ag1 | 604 | 549 |
| M11-Anti-Ag1 | 1470 | 1336 |
| CM11-Anti-Ag1 | 939 | 853 |
| Vel-Anti-Ag1 | 1040 | 946 |
| Fos-Jun-Anti-Ag1 | *N/A | — |

TABLE 6

Kd values of masked antibodies binding to SW780 cells

| Antibody | Kd (nM) | Fold change |
|---|---|---|
| Anti-Ag1 | 1.15 | — |
| A2B1-Anti-Ag1 | 134 | 116 |
| CA2B1-Anti-Ag1 | 116 | 101 |
| M15-Anti-Ag1 | *N/A | — |
| CM15-Anti-Ag1 | 177 | 153 |
| M11-Anti-Ag1 | 533 | 463 |
| CM11-Anti-Ag1 | 249 | 216 |
| Vel-Anti-Ag1 | 290 | 252 |
| CVel-Anti-Ag1 | 292 | 252 |
| Fos-Jun-Anti-Ag1 | *N/A | — |

TABLE 7

Kd values of masked antibodies binding to HT1080 cells

| Antibody | Kd (nM) | Fold change |
|---|---|---|
| Anti-Ag2 | 21.0 | — |
| A2B1-Anti-Ag2 | *N/A | — |
| CA2B1-Anti-Ag2 | >2000 | >95 |
| M15-Anti-Ag2 | >2000 | >95 |
| CM15-Anti-Ag2 | >2000 | >95 |
| M11-Anti-Ag2 | 2000 | 95 |
| CM11-Anti-Ag2 | >2000 | >95 |
| Vel-Anti-Ag2 | >2000 | >95 |
| CVel-Anti-Ag2 | 2000 | 95 |
| A4B4-Anti-Ag2 | *N/A | — |

TABLE 8

Kd values of masked antibodies binding to HCT116 Cells

| Antibody | Kd (nM) | Fold change |
|---|---|---|
| Anti-Ag2 | 7.8 | — |
| A2B1-Anti-Ag2 | *N/A | — |
| CA2B1-Anti-Ag2 | >2000 | >256 |
| M15-Anti-Ag2 | >2000 | >256 |
| CM15-Anti-Ag2 | >2000 | >256 |
| M11-Anti-Ag2 | >2000 | >256 |
| CM11-Anti-Ag2 | 2000 | 256 |
| Vel-Anti-Ag2 | >2000 | >256 |
| CVel-Anti-Ag2 | >2000 | >256 |
| A4B4-Anti-Ag2 | *N/A | — |

TABLE 9

Kd values of masked antibodies binding to SW780 Cells

| Antibody | Kd (nM) | Fold change |
|---|---|---|
| Anti-Ag2 | 9.6 | — |
| A2B1-Anti-Ag2 | *N/A | — |
| CA2B1-Anti-Ag2 | 800 | 83 |
| M15-Anti-Ag2 | >2000 | >208 |
| CM15-Anti-Ag2 | >2000 | >208 |
| M11-Anti-Ag2 | >2000 | >208 |
| CM11-Anti-Ag2 | >2000 | >208 |
| Vel-Anti-Ag2 | >2000 | >208 |
| CVel-Anti-Ag2 | >2000 | >208 |
| A4B4-Anti-Ag2 | *N/A | — |

Example 2: Masking Activities of Different Coiled Coil Peptides

Table 10 shows the fold decrease in binding for different coiled coil forming peptide pairs incorporated into different antibodies and tested on different cell lines. Activity was tested using the hBU12 antibody, cAg-1, 1C1, HuMab-CD74-011, and an antibody against Antigen 2, designated hAg-2. Greater than 100 fold masking was observed for hBU12ec on aji, cAg-lec on Ramos, and hAg-2 on Raji.

TABLE 10

| Masking activities of different coiled coil peptides | | | | | |
|---|---|---|---|---|---|
| Coil Name | hBU12ec (Raji) | cAg-1 ec (Ramos) | 1C1ec (against EphA2) (PC3) | hAg-2 (Raji) | HuMab-CD74-011 (Daudi) |
| Hinge | 269 | 45 | 0.6 | 28 | 14 |
| A3B3 | 83 | 34 | 2 | | |
| A4B4 | >300 | 927 | 2.2 | >190 | 6.1 |
| CVel | >300 | 1068 | 43 | >190 | 26 |
| antipO | 38 | 26 | 0.9 | | |
| dHLX | >300 | 233 | 16 | | |
| Vel | | 740 | | >125 | |
| A2B1 | | 221 | | >125 | |
| M15 | | 496 | | >125 | |
| M11 | | 390 | | >125 | |
| Fos/Jun | | 218 | | | |
| Cys-A2B1 | | 225 | | >125 | |
| Cys-M15 | | 499 | | >125 | |
| Cys-M11 | | 691 | | >125 | |
| Cys-Fos/Jun | | 1027* | | | |

Example 3: Cleavage Activity of Different Protease Sites by Different Proteases The MMPs were all activated via incubation with 1.25 mM 4-aminophenyl mercuric acetate (APMA) at 37 C for 1 hour up to 24 hours. Legumain was activated via 2 hour incubation at 37° C. in 50 mM sodium acetate, 100 mM NaCl, pH 4.0.

To assess the cleavage profile of the cleavage sequences, antibodies (10 μg) were incubated overnight at 37° C. with 400 pmol/min normalized proteases as indicated by manufacturer's reported values. Cleavage was assessed using Waters Acquity/Xevo UPLC where the cleaved and uncleaved fragments were reduced using excess DTT and separated using a PLRP-MS 3 μm column (Agilent) and analyzed using UNIFI (Waters). As shown in FIG. 5, PLRP-MS was used to determine cleavage of peptide sequence. CVel anti-antigen 1 light chain has a calculated mass of 29639.9 Da and an observed mass of 29640.2 Da. Cleaved anti-antigen 1 light chain has a calculated mass of 24623.3 Da and the observed mass was 24623.8 Da.

The protease cleavage profile of three protease cleavage sites (MMP #1, MMP #2 and CytomX) were tested against a panel of tumor-associated proteases such as human and murine/rat MMPs, the ADAMs family, uPA, matriptase, and legumain. Additionally, the cleavage of the sequences by extracellular proteases tPA and Factor Xa were tested. The protease cleavage profiles at these three protease cleavage sites are shown in Table 11.

The peptides (N-terminally fused to the hBU12 antibody backbone) were incubated at 37° C. overnight with 400 pmol/min normalized protease and assessed for cleavage. MMP #1 was cleaved by the majority of the MMPs as well as uPA and Matriptase. MMP #2 was cleaved by almost all MMPs except MMP13 and was untouched by other protease classes. The CytomX sequence was only cleaved by uPA, matriptase, and legumain. Together this data suggest that MMP #1 is more promiscuous among protease classes in comparison to the other two protease cleavage sites.

For all cleaved antibodies used in binding or cytotoxicity assays, masked antibody (50-250 µg) was incubated overnight at 37° C. with activated human MMP2 (1 µg).

TABLE 11

Protease cleavage profiles at three protease cleavage sites

| | Cleavage Sequence: | | |
|---|---|---|---|
| Enzyme | MMP#1 GPLG*VR | MMP#2 IPVS*LR | CytomX LSGR*SDNH |
| Human MMP2 | Complete | Complete | None |
| Human MMP7 | Complete | Complete | None |
| Human MMP9 | Complete | Complete | None |
| Human MMP13 | Complete | Minimal | None |
| Murine MMP2 | Complete | Partial | None |
| Murine MMP7 | Partial | Complete | None |
| Rat MMP9 | Partial | Complete | None |
| Upa | Partial | None | Complete |
| Matriptase | Complete | Minimal | Complete |
| Legumain | None | Minimal | Complete |
| tPA | — | None | None |
| Factor Xa | Minimal | None | None |
| ADAMs (hu, mu) | None | None | None |

Example 4: Changes in pI on Masking Antibodies

Antibodies were buffer exchanged into 10 mM sodium phosphate pH 6.5 and diluted to a working concentration of 2 mg/mL. The sample was diluted into a solution containing urea, carrier ampholytes, methyl cellulose, and two pI markers at pI 6.14 and 9.5. The samples were analyzed using an iCE3 Capillary IEF System (Protein Simple) and the isoelectric point calculated using the two standards. The isoelectric point (pI) was measured in order to assess the potential perturbations to additional of the masking domains. Table 12 shows the calculated and measured pI of masked hBU12ec (anti-cd19) antibodies compared with a control hBU12ec antibody. The measured pI of the parent antibody (8.3) was increased by the addition of the Hinge blockers (8.7-8.8) as well as the A4B4 and dHLX coiled coils (9.1). The CVel coil decreased the pI to 7.2. Generally, the pI of the masked hBU12 antibodies were within 1 unit of the parent. The anti-Ag-1 masked antibodies all had pI values between 7.7 and 8.8 where the N-terminally linked coiled coils generally had a lower pI than their un-linked counterparts as shown in Table 13.

TABLE 12

Changing pIs on masking antibodies with varying coiled coil forming peptides

| Sample | pI of Main Peak | Calculated |
|---|---|---|
| hBU12ec (Control) | 8.3 | |
| HgM2 hBU12ec V6 | 8.8 | 8.2 |
| HgNC hBU12ec | 8.7 | 8.2 |
| A4B4 hBU12ec | 9.1 | 8.5 |
| CVel hBU12ec | 7.2 | 7.1 |
| dHLX hBU12ec | 9.1 | 8.5 |

TABLE 13

Changes in pI for coiled coil forming peptides linked to cAg-1 ec.

| Sample | pI of Main Peak |
|---|---|
| A2B1 cAg-1 ec | 8.3 |
| M11 cAg-1 ec | 8.8 |
| M15 cAg-1 ec | 8.2 |
| FJ cAg-1 ec | 8.6 |
| Vel cAg-1 ec | N/A* |
| CA2B1 cAg-1 ec | 7.7 |
| CM11 cAg-1 ec | 8.2 |
| CM15 cAg-1 ec | 7.7 |
| CFJ cAg-1 ec | 7.9 |
| CVel cAg-1 ec | 7.1 |
| CA4B4 cAg-1 ec | 8.5 |

Example 5: Pharmacokinetics (PK) Values of Masked Antibodies

Pharmacokinetics (PK) experiments were performed using radiolabeled antibodies. Antibodies (1 mg) were incubated with 55 µCi N10 succinimidyl propionate, [propionate-2,3-3H]—(Moravek Biochemicals, Brea, Calif., 80 Ci/mmol, 1 mCi/ml, 9:1 hexane:ethyl acetate solution) for 2 hours at RT at pH 8.0. The mixture was centrifuged at 4,000×g for 5 minutes and the lower aqueous layer was moved. The aqueous layer was diluted and concentrated four times using Amicon Ultra-15 Centrifugal Filter Units (Millipore, Cat. No.: UFC903024, 30 kDa MWCO) to remove excess radioactive material. The radiolabeled antibodies were filtered through sterile 0.22 µm Ultrafree-MC Centrifugal Filter Units (Millipore, Billerica, Mass.) and the final antibody or ADC concentration was measured spectrophotometrically. The specific activity (µCi/mg) of each product was determined by liquid scintillation counting. The radiolabeled antibodies were injected at 0.5 mg/kg in Balb/C mice via tail vein (six animals per dose group, randomly assigned). The blood was drawn into K2 EDTA tubes via saphenous vein at various time points and processed to plasma. Plasma samples were added to Ecoscint-A liquid scintillation cocktail (National Diagnostics), and the total radioactivity was measured via liquid scintillation counting. The specific activity of the radiolabeled samples was used to calculate the antibody concentration at each time point.

The PK of various hinge and coiled-coil masked hBU12 antibodies were assessed in Balb/C mice. The antibodies were injected at 0.5 mg/kg and the total antibody found in plasma was measured. The masked hBU12 antibodies displayed similar PK to the parent with the exception of dHLX hBU12.

FIG. 2 shows concentrations of antibodies versus time for various coiled coil masked antibodies incubated in plasma as compared with an hBU12ec control. Most of the coiled coil masked antibodies showed similar pharmacokinetic behavior to the control.

Example 6: Preparation of Masked Antibody Drug Conjugates (ADC) and Cytotoxicity Assay Antibody, antibody interchain disulfides were reduced with an excess of TCEP (20 eq, pH 8, 37° C., 90 minutes), which was removed via buffer exchange with Amicon spin filters (EMD Millipore UFC503096). The disulfides were re-oxidized (with the exception of engineered thiols) using dehydroascorbic acid (Sigma Aldrich 261556) (20 eq, pH 7.4, RT, 45 minutes, 2 additions). Excess dehydroascorbic acid was removed via three rounds of dilution and concentration in Amicon spin filters. Propylene glycol was added to the reaction mixture to a final concentration of 50%. A solution of PBD-linker (3 eq) was diluted with propylene glycol and added to the re-oxidized antibody (leq) containing two free thiols at position 239. The reaction was allowed to proceed for 30 minutes then treated with a slurry of activated charcoal in water for 30 minutes. The activated charcoal was removed via filtration and the reaction was further purified using a Nap5 column (GE Healthcare Life Sciences, 17-0853-02). For mixed 4-load mc-MMAF ADCs, antibody interchain disulfides were partially reduced using 2.1 equivalents of TCEP at pH 8 for 60 min. Excess TCEP was then removed by two rounds of dilution and concentration. At that time, 4.4 molar equivalents of drug-linker was added to the partially reduced antibody. Following conjugation excess drug-linker was removed using quadrasil MP thiol resin for 15 min, followed by desalting into PBS, pH 7.4 using a PD-10 gel filtration column. For all ADCs, drug-loading was determined by PLRP-MS and the extent of aggregation was determined by size exclusion chromatography.

Cell viability assays were performed using RealTime-Glo (Promega). Ramos cells (700 cells/well) were seeded onto a 96-well culture plate with a clear bottom in culture medium according to vendor protocol. Dilutions of PBD-conjugated ADC were added to each well (1000 ng/mL to 0 ng/mL) and the samples were incubated for 138 hours at 37° C. Luminescence was measured using a plate reader (Envision 4605). The data was fit using GraphPad Prism6 and an $IC_{50}$ was calculated. The $IC_{50}$ values were used to compare changes in cytotoxicity of parent ADC against masked ADC.

Table 14 shows binding and cytotoxicity data for masked ADC's compared with a control ADC. The cytotoxicity of coiled coil masked antibodies was reduced to a similar extent as the binding to Raji or Ramos cells. Cytotoxicity was restored to the same level within experimental error as the control antibody on removing masking.

Masked hBU12 antibodies (Hinge, A4B4, CVel) were conjugated to Pyrrolobenzodiazepine (PBD) to make masked-ADCs. The binding for the masked ADCs was assessed using competition FACs. The data showed that addition of the PBD did not affect blocking ability. The masked antibodies had a >100 decrease in binding in comparison to the parent. When the masking domain was cleaved, the binding was restored to approximately 2-fold of the parent.

The cytotoxicity assay displayed a distinction between the Hinge-blocked and two coiled-coil blocked ADCs. The Hinge hBU12 had a decrease in cytotoxicity of 156-fold compared to the >100 fold in the binding data. The A4B4 hBU12 ADC had a 490-fold decrease in cytotoxicity compared to the >60 decrease in binding and the CVel hBU12 ADC displayed a 1317-fold decrease in cytotoxicity in comparison to the >160 change in binding. Upon cleavage of the CVel masking domain, the cytotoxicity is restored to 1.2 fold of the parent ADC. For the hBU12 ADCs, the decrease in binding correlates well with the decrease in cytotoxicity.

TABLE 14

Cytotoxicity assays on masked antibodies

| ADC | Raji (NHL) - 100k copies/cell Binding Data | | Ramos (NHL) - 43k copies/cell Cytotoxicity Data $IC_{50}$ (ng/mL) | Fold Change |
|---|---|---|---|---|
| hBU12ec-1910(2) | | | 0.1 | |
| Hinge_v2-1910(2) | >300 | >100 | 12 | 156 |
| A4B4-1910(2) | >600 | >160 | 37 | 490 |
| Cvel-191100(2) | >600 | >160 | 100.4 | 1317 |
| Re-activated Cvel-1910(2) | | | 0.12 | 1.2 |

Example 7: Ex Vivo Zymography of Masked Antibodies

FIG. 3 shows a tumor tissue sample contacted by a masked antibody. The antibody is unmasked proximate to tumor cells expressing a protease effective to unmask the antibody. The unmasked antibody results in tumor specific staining.

Harvested tumors from xenografted mice were frozen in OCT cryo embedding media and cryosectioned (5 μm). The sections were blocked with heat inactivated human serum, washed, and incubated with AF647-labeled antibodies. The tumor slices were pre-treated with a protease cocktail for 1 hour (1:100 PCIII and 50 μm Galardin) as a control for protease activity or with PBS. The antibodies were incubated at RT for 1 hour, washed three times with TBST, and sealed with mounting medium containing DAPI (ThermoFisher, P36962). The tumor slices were then visualized using a fluorescence microscope (Olympus) and assessed for binding of AF647 labeled antibody.

To assess the tumor-associated protease cleavage of the masked antibodies, an ex vivo approach was utilized in order to assess MMP activity. Fluorescently labeled hAg-2 and CVel hAg-2 were incubated on HT1080 tumor slices. After incubation, the slices were visualized for binding via fluorescence signal. CVel hAg-2 bound to the tumor slice to a similar extent as the parent antibody. Pretreatment of the tumor slice with protease inhibitors abrogated the binding of CVel hAg-2. This data suggest that binding of the masked antibodies is protease dependent.

Mice implanted with HT1080 xenografts were dosed at 5 mg/kg of each antibody (hAg-2, CVelAg-2, VelAg-2). Tumors were harvested 1, 3, and 5 days post dose. At given time points (1, 3, 4 days), mice were sacrificed and tissues and plasma collected. Tissues were homogenized and human antibody was purified from biological samples using IgSelect resin. Captured antibody was reduced and separated by SDS-PAGE, then probed by Western blot using an HRP-conjugated anti-human Fc antibody. The percent cleaved antibody was assessed by densitometry of bands corresponding to masked and unmasked heavy chains, which differ in size by about 5 kDa. Very little unmasked antibody (<5%) was detected in plasma or liver at any timepoints tested.

FIGS. 6A and 6B display cleavage of the CVel and Vel-blocked hAg-2 antibodies in the indicated tissue. The cleavage of the antibodies was separated into the three separate mice for each time point. The fourth mouse did not contain a tumor. At day 3, VelhAg-2 displayed more cleavage in comparison to the CVelhAg-2 construct. Additionally, there was higher cleaved product in the tumor compared to normal tissues. At Day 4, the VelhAg-2 showed consistent, robust cleavage of the masked construct in comparison to more variable cleavage observed for CvelhAg-2.

Example 8: Studies on Vel-Masked Anti-CD19 Antibody-Drug Conjugates (ADCs)

The binding of unmasked and Vel-masked anti-CD19 ADCs with varying cleavage sequences were tested by flow cytometry using CD19-positive Ramos cells. The bound antibody was detected using a fluorophore-labeled anti-human secondary antibody as shown in FIG. 8A.

The anti-proliferative activity of anti-CD19 ADCs was evaluated on CD19-positive Ramos cells. Ramos cells were incubated for 96 hours with ADCs, and impacts to cell proliferation was assessed using Cell Titer Glo (Promega) as shown in FIG. 8B.

The antitumor activity of unmasked and Vel-masked anti-CD19 antibody-drug conjugates was tested in a Ramos xenograft model in NSG mice. All ADCs were administered by intraperitoneal injection at a dose of 6 mg/kg. The results are shown in FIG. 8C.

Example 9: Studies on Masked Anti-Mouse CD3 Antibody 145-2C11

The masking of anti-mouse CD3 antibody 145-2C11 was achieved using the Vel-IPV sequence. The binding was assessed using CD3(+) HT-2 cells by flow cytometry. A fluorophore-labeled anti-mouse Fc antibody was used for detection of bound antibodies. When the anti-mouse CD3 antibody was masked by Vel-IPV, a minimal antibody binding was observed as shown in FIG. 9A.

Masking with VEL-IPV improved the target-mediated drug disposition of 145-2C11 in BALB/c mice. Antibodies were labeled with $^3$H-proprionate via lysine conjugation and were administered to BALB/c mice at an IV dose of 1 mg/kg. Antibody concentration was determined by scintillation counting of plasma drawn at different timepoints. The concentration of 145-2C11 in plasma was below detectable amounts within 2 days post-dose, whereas Vel-IPV-145-2C11 concentrations could be measured up to 14 days post-dose as shown in FIG. 9B.

The mitigation of cytokine release by anti-CD3 antibody 145-2C11 (with a mIgG2a backbone) was assessed by IV injection in BALB/mice. Mice were injected with 25 micrograms of antibody and serum cytokine levels were determined at a series of timepoints <24 hours post-dose. Significant decreases in IFN-gamma and IL-2 were detected for masked anti-CD3 antibody compared to unmasked 145-2C11 as shown in FIG. 9C-D.

Example 10: Studies on Masked Anti-Human and Anti-Mouse Ag2 Antibodies

The stability of masked anti-human-Ag2 antibodies bearing different coiled coil domains was assessed using intravenous administration to BALB/c mice. Antibodies were dosed at 5 mg/kg. At the given time point (3 days), plasma was collected from dosed mice. Human antibody was purified from plasma using IgSelect resin. Captured antibody was reduced and separated by SDS-PAGE, then probed by Western blot using an HRP-conjugated anti-human Fc antibody. The percent cleaved antibody was assessed by densitometry of bands corresponding to masked and unmasked heavy chains, which differ in size by about 5 kDa. As shown in FIG. 10, M15 is not stable as compared to CM15. There is no significant difference between A2B1 and CA2B1. The difference between Vel and CVel is not distinct.

A mouse reactive anti-Ag2 antibody could be masked using the same Vel and IPV sequence used on the human Ag2 antibody. Masking with these constructs blocked antibody binding to murine Ag2 positive cells as shown in FIG. 11A.

The anti-mouse Ag2 antibody drives depletion of platelets in BALB/c mice when administered at a single IV dose of 10 mg/kg. In contrast, this depletion was not observed when mice were administered Vel-IPV-Anti-Ag2 at a dose of 10 mg/kg IV. The results are shown in FIG. 11B.

The masked anti-mouse Vel-IPV-Ag2 antibody improved pharmacokinetics in plasma of BALB/c mice compared to unmasked Anti-Ag2, demonstrating that the masked antibody is able to avoid target-mediated drug disposition. Vel-IPV-Anti-Ag2 and Anti-Ag2 antibodies were labeled with $^3$H-proprionate via lysine conjugation and were administered to BALB/c mice at an IV dose of 1 mg/kg. Antibody concentration was determined by scintillation counting of plasma drawn at different timepoints. The concentration of Anti-Ag2 in plasma was below detectable amounts within 15 min, whereas Vel-IPV-Anti-Ag2 concentrations could be measured up to 7 days post-dose. The results are shown in FIG. 11C.

The anti-mouse Ag2 antibody drove antitumor activity in the A20 lymphoma model but caused concomitant depletion of peripheral Ag2(+) cells. The masked Vel-IPV-Anti-Ag2 antibody conferred similar activity but abrogated effects on cell depletion. The Vel-IPV-Anti-Ag2 antibody avoided the peripheral antigen sink but maintained tumor binding. The results are shown in FIGS. 12A-D.

To test the ability of masking to improve pharmacokinetics and tolerability of anti-Ag2 IgG1 antibody variants, a series of IV single dose studies were conducted in cynomolgus macaques. The anti-Ag2 IgG1 antibodies tested were cross-reactive with human and cyno Ag2 that is highly conserved across these species in expression and sequence. Evaluation of protease activity by in situ gel zymography of a panel of cynomolgus macaque and human tissues indicated protease activity levels were also highly conserved across these species. Therefore, the cynomolgus macaque represents a relevant species for evaluating the impact of masking on Anti-Ag2 antibody pharmacokinetics and tolerability.

Pharmacokinetics of Anti-Ag2 and Vel-IPV-Anti-Ag2 were assessed using a generic total antibody (TAb) ELISA. The generic TAb ELISA uses 96-well microtiter plates coated with anti-human light chain kappa mAb that binds to human light chain kappa of Anti-Ag2 and Vel-IPV-Anti-Ag2. It does not cross-react with cynomolgus monkey light chain kappa. Study samples were diluted into the dynamic range of the assay for Anti-Ag2 (10 (LLOQ) to 1280 ng/mL (ULOQ)) or Vel-IPV-Anti-Ag2 (20 (LLOQ) to 2560 ng/mL (ULOQ)) with naive pooled cynomolgus monkey K$_2$EDTA plasma. The diluted samples, along with QCs and calibrators, were subjected to a Minimum Required Dilution (MRD) of 1:20 with assay buffer prior to addition to the blocked and washed plates. After incubation for 1 hour at RT, the plates were washed and bound analyte was detected with biotinylated anti-human light chain kappa mAb (identical clone as the capture reagent) followed by the addition of polymer horseradish peroxidase conjugated to streptavidin (poly-HRP-SA). Subsequent to incubation and washing, the HRP substrate 3,3',5,5'-tetramethyl-benzidine (TMB) was added to the plates and the color developed for 10 minutes. The reaction was stopped with 1N HCl and the plates were read on a Spectromax M5 plate reader at 450 nm-630 nm. The net absorbance values were imported into Watson LIMS v. 7.4.2 and a 5-PL nonlinear regression was performed for conversion of absorbance to ng/mL total antibody present in the samples. The result is shown in FIG. 13A.

Anti-Ag2 antibody results in depletion of cells expressing Ag2 in the periphery of cynomolgus macacques. The impacts of masking of Anti-Ag2 using Vel-IPV was assessed by comparing the depletion of these peripheral Ag2(+) cells by cell counting. At a dose of 1 mg/kg Anti-Ag2 caused a pronounced decrease in peripheral Ag2(+) cells, whereas administration of Vel-IPV-Anti-Ag2 lead to minimal changes in the same cell population. A 10 mg/kg dose of Vel-IPV-Anti-Ag2 provided a similar pharmacodynamic effect as the 1 mg/kg dose of Anti-Ag2. The result is shown in FIG. 13B.

Anti-Ag2 antibody also mediates production of cytokines, such as IL10. The impacts of masking on cytokine production were assessed via Luminex multi-cytokine panel analysis of serum from cynomolgus macacques at various timepoints. Significantly diminished production of IL10 was observed for Vel-IPV-Anti-Ag2 compared to unmasked antibody. The result is shown in FIG. 13C.

Anti-Ag2 antibody drives antitumor activity in L428 xenografts when dosed four times at 1 mg/kg intravenously given every 4 days. The antitumor activity of Vel-Anti-Ag2 antibodies with different protease-cleavable linker sequences were compared in the L428 xenograft model. Vel-Anti-Ag2 containing an intended MMP-cleavable sequence -PLGLAG- provided a similar antitumor effect as unmasked antibody. Meanwhile, a Vel-Anti-Ag2 antibody containing a scrambled sequence -LALGPG- provided attenuated antitumor activity. Of note, both of the Vel-masked Anti-Ag2 antibodies bound to L428 cells in vitro, indicating that differential in vivo activity is not due to differences in binding for the two different masked antibodies. The results are shown in FIGS. 14A and 14B.

What is claimed is:

1. A bivalent antibody comprising two light and heavy chain pairs, wherein the N-termini of the light and heavy chains of at least one of the pairs are linked, via linkers comprising a protease cleavage site, to coiled-coil forming peptides that associate to form a coiled coil reducing binding affinity of the antibody to a target relative to the binding affinity of the antibody in naked form; wherein (a) a peptide comprising the sequence QGASTSVDELQAEVDQLEDENYALKTKVAQLRKKVEKLGSIPVSLRSG (SEQ ID NO: 34) provides the linker comprising the protease cleavage site and the coiled-coil forming peptide linked to the light chain and a peptide comprising the sequence QGASTTVAQLEEKVKTLRAENYELKSEVQRLEEQVAQLGSIPVSLRSG (SEQ ID NO: 31) provides the linker comprising the protease cleavage site and the coiled-coil forming peptide linked to the heavy chain; or (b) a peptide comprising the sequence QGASTTVAQLEEKVKTLRAENYELKSEVQRLEEQVAQLGSIPVSLRSG (SEQ ID NO: 31) provides the linker comprising the protease cleavage site and the coiled-coil forming peptide linked to the light chain and a peptide comprising the sequence QGASTSVDELQAEVDQLEDENYALKTKVAQLRKKVEKLGSIPVSLRSG (SEQ ID NO: 34) provides the linker comprising the protease cleavage site and the coiled-coil forming peptide linked to the heavy chain.

2. The bivalent antibody of claim 1, wherein the light and heavy chains of both of the pairs are linked via the linkers comprising the protease cleavage site to the coiled-coil forming peptides that associate to form a coiled coil reducing binding affinity of the antibody to the target.

3. The bivalent antibody of claim 1, conjugated to a cytotoxic or cytostatic drug.

4. The bivalent antibody of claim 3, conjugated to a cytotoxic or cytostatic drug via a cysteine residue of the bivalent antibody.

5. The bivalent antibody of claim 1, wherein the two light and heavy chain pairs are the same.

6. The bivalent antibody of claim 1, wherein the two light and heavy chain pairs are different.

7. The bivalent antibody of claim 6, wherein the two light and heavy chain pairs have specificity for different targets.

8. The bivalent antibody of claim 6, wherein the two light and heavy chain pairs have specificity for the same target.

9. The bivalent antibody of claim 7, wherein one and only one of the pairs are linked via the linkers comprising the protease cleavage site to the coiled-coil forming peptides that associate to form a coiled coil reducing binding affinity of the antibody to the target.

10. The bivalent antibody of claim 1, wherein the heavy chain comprises a constant region comprising CH1, hinge, CH2 and CH3 regions.

11. The bivalent antibody of claim 1, wherein the target or one of the targets is any of CD19, CD30, LIV-1, CD70, or CD74.

12. The bivalent antibody of claim 1, wherein the binding is reduced 100-1000 fold relative to that of the antibody in naked form.

13. The bivalent antibody of claim 1, wherein the binding is reduced 100-500 fold relative to that of the antibody in naked form.

14. The bivalent antibody of claim 3, wherein cytotoxicity of the conjugate is reduced at least 100-1000 fold relative to that of the antibody in naked form.

15. The bivalent antibody of claim 3, wherein cytotoxicity of the conjugate is reduced 100-500 fold relative to that of the antibody in naked form.

16. The bivalent antibody of claim 1, wherein multiple copies of the coiled coil forming peptide are linked in tandem to the N-termini of the heavy and light chains.

17. The bivalent antibody of claim 1, wherein a peptide consisting of the sequence QGASTSVDELQAEVDQLEDENYALKTKVAQLRKKVEKLGSIPVSLRSG (SEQ ID NO: 34) provides the linker comprising the protease cleavage site and the coiled-coil forming peptide linked to the light chain and a peptide of consisting of the sequence QGASTTVAQLEEKVKTLRAENYELKSEVQRLEEQVAQLGSIPVSLRSG (SEQ ID NO: 31) provides the linker comprising the protease cleavage site and the coiled-coil forming peptide linked to the heavy chain.

18. The bivalent antibody of claim 1, wherein a peptide consisting of the sequence QGASTTVAQLEEKVKTLRAENYELKSEVQRLEEQVAQLGSIPVSLRSG (SEQ ID NO: 31)) provides the linker comprising the protease cleavage site and the coiled-coil forming peptide linked to the light chain and a peptide consisting of the sequence QGASTSVDELQAEVDQLEDENYALKTKVAQLRKKVEKLGSIPVSLRSG (SEQ ID NO: 34) provides the linker comprising the protease cleavage site and the coiled-coil forming peptide linked to the heavy chain.

19. The bivalent antibody of claim 7, wherein one of the targets is a surface antigen on an immune cell and the other is a surface antigen on a cancer cell.

20. The bivalent antibody of claim 19, wherein the surface antigen on the immune cell is CD3.

* * * * *

UNITED STATES PATENT AND TRADEMARK OFFICE
CERTIFICATE OF CORRECTION

PATENT NO. : 11,230,610 B2
APPLICATION NO. : 16/348481
DATED : January 25, 2022
INVENTOR(S) : Vivian Trang et al.

It is certified that error appears in the above-identified patent and that said Letters Patent is hereby corrected as shown below:

In the Claims

Column 83, Claim 1, Line 21:
Delete "coiled coil" and insert --coiled-coil--

Column 83, Claim 2, Line 46:
Delete "coiled coil" and insert --coiled-coil--

Column 83, Claim 9, Line 63:
Delete "coiled coil" and insert --coiled-coil--

Column 84, Claim 14, Line 30:
Delete "at least"

Column 84, Claim 16, Line 36:
Delete "coiled coil" and insert --coiled-coil--

Column 84, Claim 18, Line 52:
Delete "31))" and insert --31)--

Signed and Sealed this
Eighteenth Day of April, 2023

Katherine Kelly Vidal
*Director of the United States Patent and Trademark Office*